(12) United States Patent
Hasegawa et al.

(10) Patent No.: US 10,262,412 B2
(45) Date of Patent: Apr. 16, 2019

(54) WELDED STATE MONITORING SYSTEM AND WELDED STATE MONITORING METHOD

(71) Applicant: NIPPON STEEL & SUMITOMO METAL CORPORATION, Tokyo (JP)

(72) Inventors: Noboru Hasegawa, Tokai (JP); Hideki Hamatani, Tokai (JP); Yoshifumi Karube, Tokai (JP); Manabu Ueda, Nagoya (JP); Michitoshi Tanimoto, Tokyo (JP); Takashi Oosawa, Hikari (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 113 days.

(21) Appl. No.: 15/116,543

(22) PCT Filed: Mar. 27, 2015

(86) PCT No.: PCT/JP2015/059662
§ 371 (c)(1),
(2) Date: Aug. 4, 2016

(87) PCT Pub. No.: WO2015/152059
PCT Pub. Date: Oct. 8, 2015

(65) Prior Publication Data
US 2016/0350902 A1    Dec. 1, 2016

(30) Foreign Application Priority Data
Apr. 3, 2014 (JP) .................................. 2014-077184

(51) Int. Cl.
*G06T 7/136* (2017.01)
*G06T 7/00* (2017.01)
(Continued)

(52) U.S. Cl.
CPC .............. *G06T 7/001* (2013.01); *B21C 37/08* (2013.01); *B23K 11/0006* (2013.01);
(Continued)

(58) Field of Classification Search
CPC ........................... G06T 7/001; G01N 21/8851
See application file for complete search history.

(56) References Cited

U.S. PATENT DOCUMENTS 5,026,979 A * 6/1991 Ortiz, Jr. ................ B23K 26/03
250/205
5,245,682 A * 9/1993 Ortiz, Jr. .................. G02B 6/32
385/33
(Continued)

FOREIGN PATENT DOCUMENTS

CA    2854097 A1    5/2013
EP    2221137 A1    8/2010
(Continued)

OTHER PUBLICATIONS

International Search Report of PCT/JP2015/059662 (PCT/ISA/210) dated Jun. 23, 2015.
(Continued)

*Primary Examiner* — Jayanti K Patel
*Assistant Examiner* — Irfan Habib
(74) *Attorney, Agent, or Firm* — Birch, Stewart, Kolasch & Birch, LLP

(57) ABSTRACT

A welded state monitoring system according to an aspect of the present invention is a welded state monitoring system used for plasma shielded electric resistance welding in which electric resistance welding is performed while irradiating a weld zone of a steel sheet with plasma, and is provided with a plasma irradiation device which irradiates the weld zone with plasma, a first image capturing device which captures an image of the weld zone from above and
(Continued)

has an image sensor capable of detecting light having a wavelength of 850 nm or more, a first wavelength region limiting device which limits light incident on the first image capturing device to a wavelength region of 850 nm or more, and an image processing device which subjects the image captured by the first image capturing device to image processing and analyzes the welded state of the weld zone thereby being able to analyze the welded state without being affected by the plasma.

9 Claims, 15 Drawing Sheets

(51) Int. Cl.
| | |
|---|---|
| *B21C 37/08* | (2006.01) |
| *B23K 11/36* | (2006.01) |
| *B23K 13/02* | (2006.01) |
| *B23K 31/12* | (2006.01) |
| *B23K 11/00* | (2006.01) |
| *G01N 21/88* | (2006.01) |
| *G02B 5/20* | (2006.01) |
| *H04N 5/247* | (2006.01) |
| *B23K 11/087* | (2006.01) |
| *B23K 101/06* | (2006.01) |
| *B23K 103/04* | (2006.01) |

(52) U.S. Cl.
CPC ...... *B23K 11/0073* (2013.01); *B23K 11/0873* (2013.01); *B23K 11/36* (2013.01); *B23K 13/025* (2013.01); *B23K 31/125* (2013.01); *G01N 21/8851* (2013.01); *G02B 5/208* (2013.01); *G06T 7/0004* (2013.01); *G06T 7/136* (2017.01); *H04N 5/247* (2013.01); *B23K 2101/06* (2018.08); *B23K 2103/04* (2018.08); *G01N 2201/10* (2013.01); *G06T 2207/30108* (2013.01); *G06T 2207/30136* (2013.01)

(56) References Cited

U.S. PATENT DOCUMENTS

| | | | | |
|---|---|---|---|---|
| 5,304,774 A * | 4/1994 | Durheim | ............... | B23K 26/032 219/121.63 |
| 5,329,089 A * | 7/1994 | McGee | .................. | B23K 10/02 219/121.45 |
| 6,060,685 A * | 5/2000 | Chou | .................. | B23K 26/032 219/121.64 |
| 6,188,041 B1 * | 2/2001 | Kim | ...................... | B23K 26/034 219/121.6 |
| 6,311,099 B1 * | 10/2001 | Jasper | .................. | B23K 26/032 219/121.6 |
| 6,710,283 B2 * | 3/2004 | Mori | ....................... | B23K 26/03 219/121.64 |
| 6,946,617 B2 * | 9/2005 | Brandt | ...................... | H05H 1/28 219/121.49 |
| 7,186,947 B2 * | 3/2007 | Connally | ............... | B23K 10/00 219/121.72 |
| 7,271,363 B2 * | 9/2007 | Lee | ........................ | H05H 1/46 219/121.36 |
| 8,164,022 B2 * | 4/2012 | Mazumder | .......... | B23K 26/032 219/121.64 |
| 8,440,933 B2 * | 5/2013 | Marcus | ................ | B23K 26/032 219/121.71 |
| 8,994,270 B2 * | 3/2015 | Koo | .................. | H01J 37/32366 315/111.11 |
| 9,492,888 B2 * | 11/2016 | Kodama | ............. | B23K 26/032 |
| 9,669,484 B2 * | 6/2017 | Holverson | ........... | B23K 9/0956 |
| 9,981,341 B2 * | 5/2018 | Mazumder | .......... | B23K 26/032 |
| 2002/0144984 A1 * | 10/2002 | Mori | ...................... | B23K 26/03 219/121.64 |
| 2005/0011867 A1 * | 1/2005 | Okuda | ................. | B23K 26/032 219/121.63 |
| 2006/0071156 A1 * | 4/2006 | Masaki | ............. | H01L 27/14621 250/226 |
| 2006/0081613 A1 | 4/2006 | Panthofer et al. | | |
| 2006/0108333 A1 * | 5/2006 | Picard | .................... | B23K 10/00 219/121.62 |
| 2008/0035615 A1 * | 2/2008 | Li | ......................... | B23K 26/32 219/121.63 |
| 2008/0087359 A1 * | 4/2008 | Zurecki | ..................... | C23C 4/02 148/511 |
| 2008/0290075 A1 | 11/2008 | Wittenbecher | | |
| 2010/0125267 A1 * | 5/2010 | Lee | ...................... | A61B 18/042 606/27 |
| 2010/0232678 A1 * | 9/2010 | Hasegawa | ............... | B21C 37/08 382/141 |
| 2010/0314543 A1 * | 12/2010 | Lee | .......................... | G01J 3/02 250/330 |
| 2011/0284508 A1 * | 11/2011 | Miura | .................. | B23K 31/125 219/121.64 |
| 2012/0125899 A1 * | 5/2012 | Oh | ....................... | B23K 26/032 219/121.64 |
| 2012/0212619 A1 * | 8/2012 | Nagamune | ........... | H04N 5/2256 348/164 |
| 2013/0256279 A1 | 10/2013 | Morikazu | | |
| 2014/0326705 A1 * | 11/2014 | Kodama | ............. | B23K 26/032 219/121.83 |
| 2015/0356351 A1 * | 12/2015 | Saylor | ..................... | G01S 17/89 348/164 |

FOREIGN PATENT DOCUMENTS

| | | | |
|---|---|---|---|
| JP | 57-165188 A | | 10/1982 |
| JP | 2008-087072 A | | 4/2008 |
| JP | 2009-000746 A | | 1/2009 |
| JP | 2011-031275 A | | 2/2011 |
| JP | 4890609 B2 | | 3/2012 |
| JP | 5079929 B2 | | 11/2012 |
| JP | 5125670 B2 | | 1/2013 |
| JP | 2013-212519 A | | 10/2013 |
| JP | 5316320 B2 | | 10/2013 |
| JP | 2014-36983 A | | 2/2014 |
| JP | 2014036983 | * | 2/2014 |

OTHER PUBLICATIONS

Written Opinion of PCT/JP2015/059662 (PCT/ISA/237) dated Jun. 23, 2015.
Extended European Search Report issued in European Application No. 15772548.2 dated Nov. 9, 2017.

* cited by examiner

WELDED STATE MONITORING SYSTEM AND WELDED STATE MONITORING METHOD

TECHNICAL FIELD OF THE INVENTION

The present invention relates to a welded state monitoring system and a welded state monitoring method.

Priority is claimed on Japanese Patent Application No. 2014-77184, filed on Apr. 3, 2014, the content of which is incorporated herein by reference.

RELATED ART

An electric resistance welded steel pipe manufactured using electric resistance welding is used as a line pipe and an oil well pipe used for mining and conveying of petroleum and natural gas. An electric resistance welded steel pipe is used as a pipe used in nuclear power plants, geothermal plants, and chemical plants, or as a pipe used in machine structures and general piping. In this manner, an electric resistance welded steel pipe is used in a wide field.

In conventional electric resistance welding, a belt-shaped coil formed of a steel sheet is continuously press-formed into a tubular shape by a number of roller groups. Induction heating by a work coil or direct electrification heating by a contact chip is performed for the tubular shaped steel sheet to heat and melt a circumferential end (butt end) of the steel sheet and to weld the circumferential end at a predetermined temperature while being pressurized by a squeeze roll, thereby manufacturing an electric resistance welded steel pipe.

In a steel sheet to be subjected to the electric resistance welding, a butt end region sandwiched between the contact chip or the work coil and the squeeze roll is referred to as a weld zone.

In such conventional electric resistance welding, since the weld zone is exposed to air when performing the electric resistance welding, oxides are generated on a surface of the weld zone. In a case where the oxides remain on the surface of the weld zone, penetrators which may cause weld defects are generated.

In Patent Documents 1 and 2, a technique in which the weld zone is irradiated with plasma in order to reduce oxides generated on the surface of the weld zone during electric resistance welding is disclosed. In the present specification, a technique in which electric resistance welding is performed while irradiating the weld zone with a plasma is called plasma shielded electric resistance welding. Plasma shielded electric resistance welding is fundamentally different from plasma welding, in which welding is performed using plasma irradiation alone, in the technical idea.

In plasma shielded electric resistance welding, a state where oxygen concentration is low can be maintained by the shielding action with respect to a butt surface due to ionized plasma gas, the reducing action due to the ionized plasma gas, or the like in processes of heating and melting the butt surface of the steel sheet by irradiating an appropriate part of the weld zone with plasma. As a result, it is possible to reduce formation of an oxide film of the butt surface which is likely to be a cause of oxide defects after the welding in a manufacturing process, and high quality welding with fewer defects becomes possible.

In Patent Documents 3 and 4, regarding conventional electric resistance welding, a technique which captures an image of a radiation pattern of a visible region in the weld zone using a color or monochromatic camera formed of CCD image sensors and analyzes a welded state by image processing has been disclosed.

PRIOR ART DOCUMENT

Patent Document

[Patent Document 1] Japanese Patent (Granted) Publication No. 4890609

[Patent Document 2] Japanese Patent (Granted) Publication No. 5316320

[Patent Document 3] Japanese Patent (Granted) Publication No. 5079929

[Patent Document 4] Japanese Patent (Granted) Publication No. 5125670

DISCLOSURE OF THE INVENTION

Problems to be Solved by the Invention

In Patent Documents 1 and 2, plasma shielded electric resistance welding is disclosed, but an image capturing technique of a welded state and an image analysis technique are not disclosed.

FIG. 18A is an image obtained by capturing an image of the radiation pattern of molten steel disclosed in Patent Documents 3 and 4 by the color or monochromatic image capturing technique in the visible region, for the weld zone of the steel sheet in conventional electric resistance welding. In FIG. 18A, a direction from left to right being a conveying direction of a steel sheet. An image of a state, where both edge parts in the circumferential direction of the steel sheet converge into a V shape, is captured.

However, in a case where the weld zone is irradiated with plasma, when the image capturing technique disclosed in Patent Documents 3 and 4 is used, as shown in FIG. 18B, a problem that brightness becomes higher due to the self-luminous light of plasma and contrast sufficient for detecting the edge part cannot be obtained occurs (see a portion surrounded by a circle). Furthermore, as shown in FIG. 18C, in a case where the weld zone is irradiated with plasma, a problem that an instantaneous light emission phenomenon caused by reaction of the plasma with sputtering or a steel material component frequently occurs, the weld zone is masked due to the light emission due to the reaction (see a portion surrounded by a circle), and an analysis of a welded state becomes significantly difficult occurs.

The present invention is made for solving the above-mentioned problems and an object thereof is to provide a welded state monitoring system and a welded state monitoring method which are used for plasma shielded electric resistance welding in which electric resistance welding is performed while irradiating a weld zone of a steel sheet with plasma, the welded state monitoring system and the welded state monitoring method being capable of analyzing a welded state without being affected by plasma.

Means for Solving the Problem

The present invention adopts the following means in order to solve the above-described problems and achieve related objectives.

(1) A welded state monitoring system according to an aspect of the present invention is a welded state monitoring system, which is used for plasma shielded electric resistance welding in which electric resistance welding is performed while irradiating a weld zone of a steel sheet with plasma, and includes a plasma irradiation device which irradiates the weld zone with plasma, a first image capturing device which captures an image of the weld zone from above and has an image sensor capable of detecting light having a wavelength of 850 nm or more, a first wavelength region limiting device which limits light incident on the first image capturing device to a wavelength region of 850 nm or more, and an image processing device which subjects the image captured by the first image capturing device to image processing to analyze a welded state of the weld zone.

(2) In the welded state monitoring system according to (1), a configuration in which a first wavelength region limiting device which limits light incident on the first image capturing device to a wavelength region of 900 nm or more may be adopted.

(3) In the welded state monitoring system according to (1) or (2), a configuration in which the image sensor has a quantum efficiency of 10% or more with respect to light in the wavelength region may be adopted.

(4) In the welded state monitoring system according to any one of (1) to (3), a configuration in which the first image capturing device has a resolution of 60 μm or less when capturing an image of a range having a width of 100 mm or more may be adopted.

(5) In the welded state monitoring system according to any one of (1) to (4), a configuration in which the image processing device obtains a geometrical V convergence point which is a point where both butt ends of the steel sheet which converge in a V shape are geometrically intersect each other and a physical abutment point where both butt ends of the steel sheet which converge in a V shape physically butt against each other may be adopted.

(6) In the welded state monitoring system according to any one of (1) to (5), a configuration which further includes a second image capturing device which has the same field of view range as that of the first image capturing device and a second wavelength region limiting device which limits light incident on the second image capturing device to only light having a wavelength of 500 nm or less, and in which the image processing device obtains a plasma irradiation position in a width direction of the steel sheet which is a direction orthogonal to a conveyance direction of the steel sheet as a relative position with respect to which the weld zone is set as a reference, on the basis of the image captured by the second image capturing device may be adopted.

(7) In the welded state monitoring system according to any one of (1) to (6), a configuration which further includes a third image capturing device which is located upstream in the conveyance direction of the steel sheet and captures an image of the weld zone from above the steel sheet and from an oblique direction from either of the left or the right in the conveyance direction of the steel, and in which the image processing device obtains the plasma irradiation position in the conveyance direction of the steel sheet as a relative position with respect to which the weld zone is set as a reference, on the basis of the image captured by the third image capturing device may be adopted.

(8) In the welded state monitoring system according to (7), a configuration which further includes a third wavelength region limiting device which limits light incident on the third image capturing device to only light having a wavelength of 500 nm or less may be adopted.

(9) A welded state monitoring method according to another aspect of the present invention is a welded state monitoring method, which is used for plasma shielded electric resistance welding in which electric resistance welding is performed while irradiating a weld zone of a steel sheet with plasma, and includes capturing an image of a weld zone from above using an image capturing device by limiting light incident on an image capturing device provided with an image sensor capable of detecting light having a wavelength of 850 nm or more to a wavelength region of 850 nm or more using the image capturing device, and analyzing, using the image processing device, a welded state of the weld zone on the basis of the image captured by the image capturing device.

Effects of the Invention

According to respective embodiments described above, it is possible to provide a welded state monitoring system and a welded state monitoring method, which are used for plasma shielded electric resistance welding in which electric resistance welding is performed while irradiating a weld zone of a steel sheet with plasma. The welded state monitoring system and the welded state monitoring method are capable of analyzing a welded state without being affected by plasma.

EMBODIMENTS OF THE INVENTION

Hereinafter, a preferred embodiment of the present invention will be described with reference to the accompanying drawings.

First Embodiment

Figure 1:
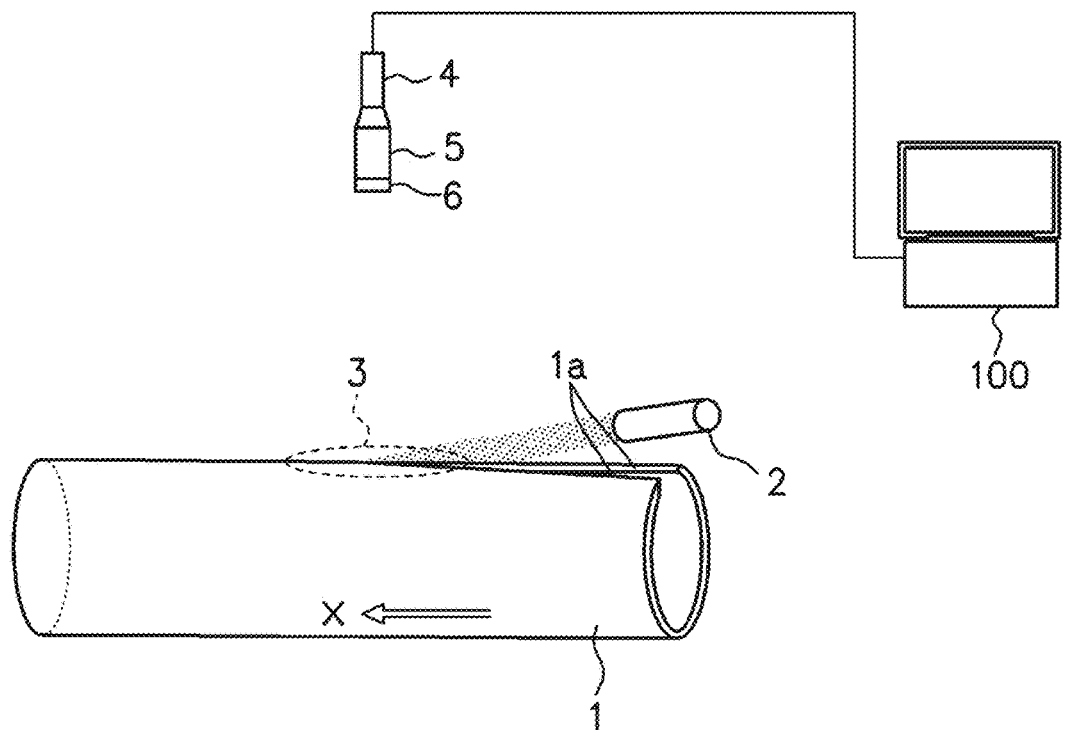
FIG. 1 is a diagram schematically showing a configuration of a welded state monitoring system in plasma shielded electric resistance welding according to the first embodiment.

In FIG. 1, a configuration of a welded state monitoring system in plasma shielded electric resistance welding according to a first embodiment is schematically shown.

In the plasma shielded electric resistance welding, a steel sheet 1 is press-formed into a tubular shape by a roll group (not shown) while conveying the steel sheet 1 from an upstream side (right side in FIG. 1) to a downstream side (left side in FIG. 1), is subjected to induction heating by a work coil or a direct electrification heating by a contact chip, and butt ends 1a of the steel sheet 1 are heated and molten.

In the present specification, a direction through which the steel sheet 1 is conveyed, that is a direction from upstream to downstream, are called a conveyance direction X of the steel sheet 1.

The steel sheet 1 is pressurized from both sides by a squeeze roll 7 (see FIG. 2A to FIG. 2E) so as to converge both butt ends 1a of the steel sheet 1 in a V shape. With this, both butt ends 1a of the steel sheet 1 are welded by butting.

A V-shaped angle formed by both butt ends 1a of the steel sheet 1 is referred to as a V-shaped convergence angle. A region which converges into the V shape formed by both butt ends 1a of the steel sheet 1 is referred to as a V-shaped convergence region.

In the butt ends 1a which is heated and molten, a surface of molten steel is oxidized and thus, an oxide is formed. Since an electromagnetic force (repulsive force) is applied to both butt ends 1a in a welding process, the oxide and the molten steel are discharged to the outside of the surface. The oxide formed on surface of the molten steel is also discharged by a pressure of the squeeze roll 7.

On the other hand, in a case where the oxide formed on the surface of the molten steel is not properly discharged in the butt ends 1a, there is a possibility that weld defects called penetrators are generated.

A plasma irradiation device 2 is arranged above the upstream of the conveyance direction X of the steel sheet 1. The plasma irradiation device 2 irradiates a weld zone 3 with plasma.

By irradiating the weld zone 3 with plasma by the plasma irradiation device 2 during the plasma shielded electric resistance welding, the weld zone 3 is covered with the plasma. In a case where $H_2$ gas is contained in plasma, as will be described in later, a reducing atmosphere is formed in the periphery of the weld zone 3.

With this, an oxygen concentration in the periphery of the weld zone 3 becomes lower and an oxide is hardly formed on the surface of the weld zone 3.

In order to irradiate the entire range of the weld zone 3 with plasma, the plasma irradiation device 2 of the present embodiment can preferably irradiate a range having a length of 100 nm or more on the steel sheet 1.

More preferably, the plasma irradiation device 2 of the present embodiment can preferably irradiate a range having a length of 200 nm or more on the steel sheet 1.

The plasma irradiation device 2 of the present embodiment irradiates plasma of a laminar flow. With this, it is possible to significantly reduce entrapment of atmospheric air into the weld zone 3 during plasma shielded electric resistance welding. For that reason, it is possible to significantly reduce formation of an oxide on the surface of the molten steel in the weld zone 3.

Power consumption of the plasma irradiation device 2 of the present embodiment is about 40 kW. This is about one tenth of power consumption of a plasma welding device.

Main components of plasma irradiated by the plasma irradiation device 2 of the present embodiment are Ar and $N_2$. The plasma irradiated by the plasma irradiation device 2 of the present embodiment may also contain $H_2$ as other component than the components in order to form the reducing atmosphere in the periphery of the weld zone 3.

Here, a camera 4 provided with an image sensor capable of detecting light having a wavelength of 850 nm or more is installed above the weld zone 3 as an image capturing device which captures an image of the weld zone 3. Also, an optical filter 6 (long wavelength pass filter) which limits light incident on the camera 4 to a wavelength region of 850 nm or more is mounted, for example, on the front surface of a lens 5 of the camera 4. In the first embodiment, the optical filter 6 corresponds to a first wavelength range limitation device in the present invention.

In the present specification, the matters that light having a wavelength of 850 nm or more can be detected means that the camera 4 has quantum efficiency of 10% or more to light having a wavelength of 850 nm or more. The camera 4 preferably has higher quantum efficiency of 20% or more, for example, to light having a wavelength of 850 nm or more.

The image sensors capable of detecting a wavelength of 850 nm or more include, for example, the CMOS, InGaAs, and InSb image sensors.

The image processing device 100 subjects the image captured by the camera 4 to image processing and analyzes a welded state of the weld zone 3. The image processing device 100 includes a computer device provided with a CPU, a ROM, and a RAM, for example.

(Welded State of Weld Zone 3)

The welded states of the weld zone 3 in the plasma shielded electric resistance welding will be described with reference to FIG. 2A to FIG. 2E.

Figure 2A:
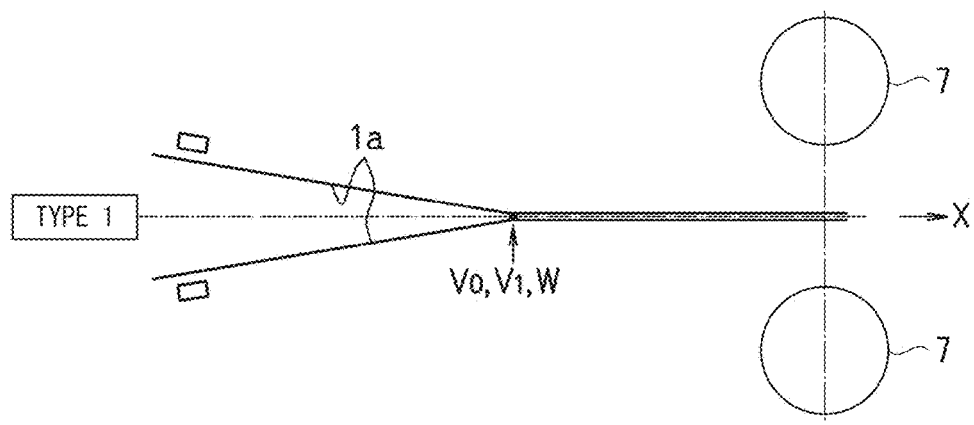
FIG. 2A is a schematic diagram showing Type 1 welded states of a weld zone in the plasma shielded electric resistance welding.
Figure 2B:
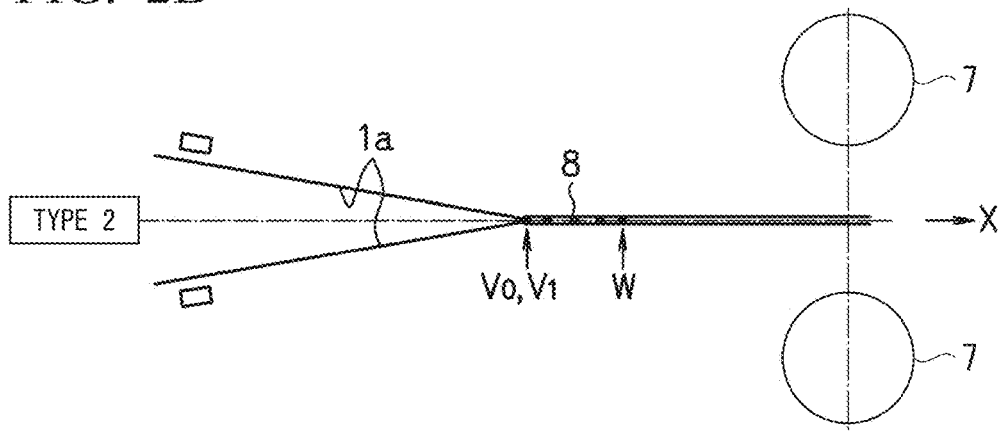
FIG. 2B is a schematic diagram showing Type 2 welded states of the weld zone in the plasma shielded electric resistance welding.
Figure 2C:
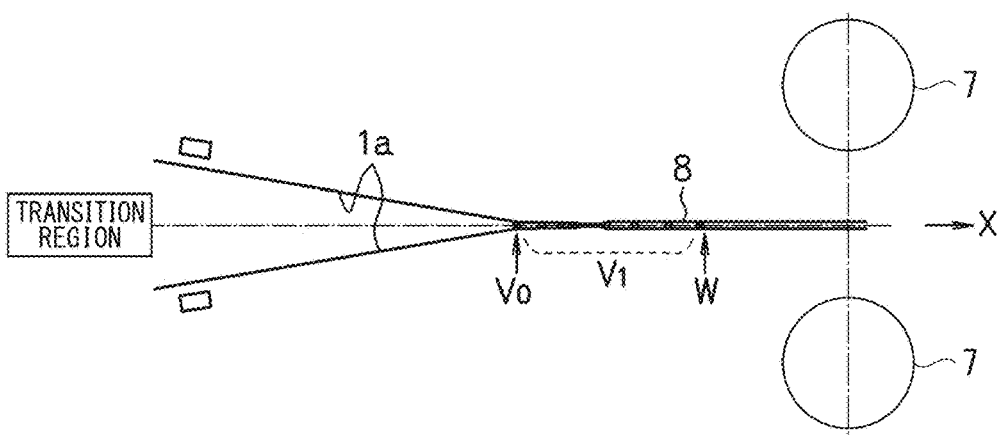
FIG. 2C is a schematic diagram showing a transition region of welded states of the weld zone in the plasma shielded electric resistance welding.
Figure 2D:
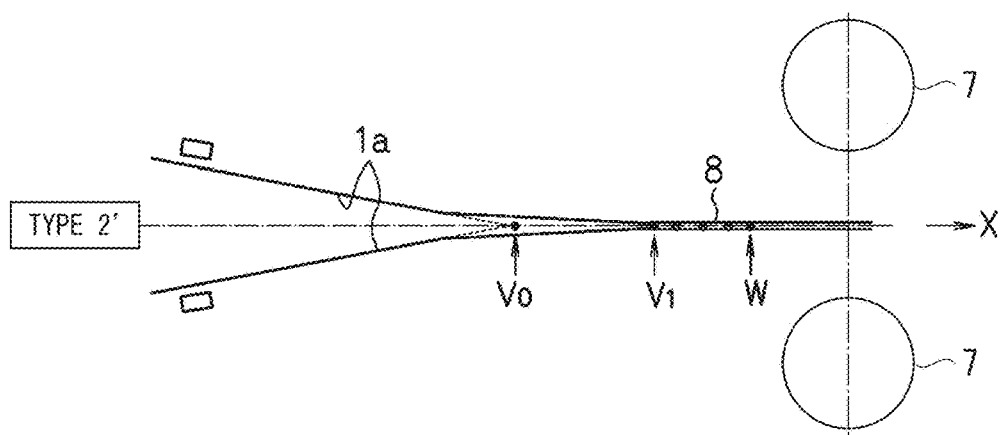
FIG. 2D is a schematic diagram showing Type 2' welded states of the weld zone in the plasma shielded electric resistance welding.
Figure 2E:
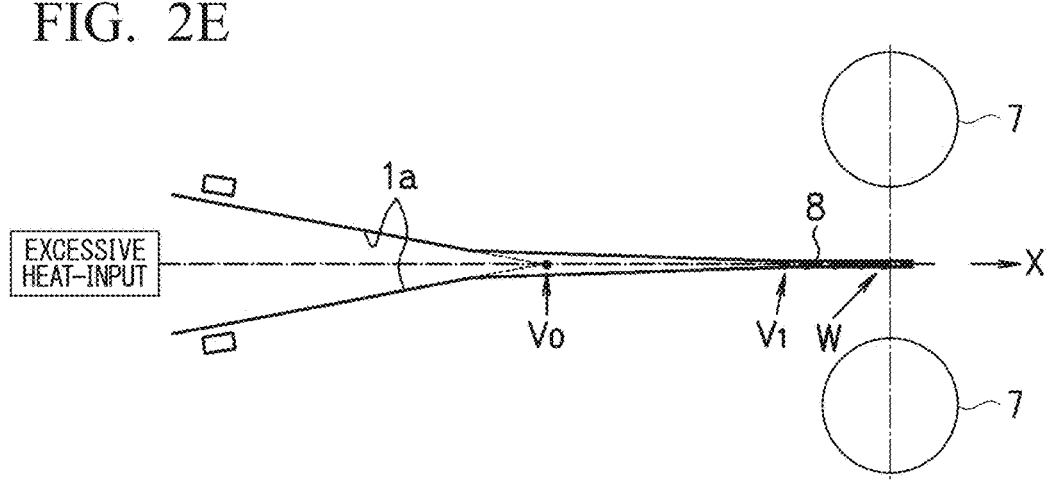
FIG. 2E is a schematic diagram showing an excessive heat-input of welded states of the weld zone in the plasma shielded electric resistance welding.

FIG. 2A is a schematic diagram showing Type 1 of welded states of the weld zone 3. FIG. 2B is a schematic diagram showing Type 2 of the welded states of the weld zone 3. FIG. 2C is a schematic diagram showing a transition region of the welded states of the weld zone 3. FIG. 2D is a schematic diagram showing Type 2' of the welded states of the weld zone 3. FIG. 2E is a schematic diagram showing an excessive heat-input of the welded states of the weld zone 3.

The amount of heat (heat-input amount) applied to the weld zone 3 is gradually increased from FIG. 2A to FIG. 2E.

The welded state of the weld zone 3 is divided into five types due to the difference in the amount of heat-input.

In a case where the heat-input amount is less than an amount of heat-input required for welding, the welded state is Type 1 shown in FIG. 2A.

In a case where the heat-input amount is proper for performing welding, the welded state is Type 2 shown in FIG. 2B.

In a case where the heat-input amount is increased to more than Type 2, the welded state is the transition region shown in FIG. 2C.

In a case where the heat-input amount is further increased from the transition region, the welded state is Type 2' shown in FIG. 2D.

In a case where the heat-input amount is further increased from Type 2', the welded state is the excessive heat-input shown in FIG. 2E.

When the welded state of the weld zone 3 in the plasma shielded electric resistance welding is observed from above, positions and separation states of three points of a geometrical V convergence point $V_0$, a physical abutment point $V_1$, and a weld point W vary by the heat-input amount.

The geometrical V convergence point $V_0$ is a point where approximate straight lines of both butt ends 1a of the steel sheet 1 converging into the V shape geometrically intersect. More specifically, when obtaining the geometrical V convergence point $V_0$, the image processing device 100 linearly approximates a portion of the butt end 1a in the image captured by the camera 4 and regards an intersecting point of a pair of approximate straight lines obtained by the linear approximation as the geometrical V convergence point $V_0$.

When the geometrical V convergence point $V_0$ is obtained, which range of the butt end 1a to be linearly approximated is determined in advance. The range of the butt end 1a to be subjected to linear approximation can be determined as an arbitrary range between the leftmost end of the butt end 1a and the physical abutment point $V_1$ in the image captured by the camera 4 in the conveyance direction X of the steel sheet 1. For example, it is possible to linearly approximate the butt end 1a in a 50% of the range between the leftmost end of the butt end 1a and the physical abutment point $V_1$.

The physical abutment point $V_1$ is a point where the both butt ends 1a of the steel sheet 1 converging into the V shape are physically butting (contacting) each other.

The weld point W is a point where discharging of the molten steel is started by rolling reduction of the squeeze roll 7.

In a case where the welded state of the weld zone 3 in the plasma shielded electric resistance welding is Type 1, three points of the geometrical V convergence point $V_0$, the physical abutment point $V_1$, and the weld point W almost overlap each other.

In a case where the welded state of the weld zone 3 in the plasma shielded electric resistance welding is between Type 2 and the excessive heat-input, the geometrical V convergence point $V_0$ is separated from the weld point W and an elongated gap called a slit 8 is generated. Furthermore, in a case where the welded state of the weld zone 3 in the plasma shielded electric resistance welding is between the transition region and the excessive heat-input, the geometrical V convergence point $V_0$ is separated from the physical abutment point $V_1$.

In a case where the welded state of the weld zone 3 in the plasma shielded electric resistance welding is Type 2', the V-shaped convergence region has a characteristic shape having a two-stage V-shaped convergence angle. As such, a phenomenon that the V-shaped convergence region has the two-stage V-shaped convergence angle is referred to as a two-stage convergence phenomenon.

In a case where the welded state of the weld zone 3 in the plasma shielded electric resistance welding is the transition region, a distance between both butt ends 1a is very short in the V-shaped convergence region formed by both butt ends 1a and the physical abutment point $V_1$. Due to this, the physical abutment point $V_1$ moves between the geometrical V convergence point $V_0$ and the weld point W.

In this case, when the physical abutment point $V_1$ is hopped to the upstream of the conveyance direction X, an electromagnetic force in the downstream of the conveyance direction X of the steel sheet 1 is dissipated. With this, there is a tendency that the oxide of both butt ends 1a is not discharged and the weld defects are increased.

In a case where the welded state of the weld zone 3 in the plasma shielded electric resistance welding is the excessive heat-input, the weld point W approaches the position of the squeeze roll 7 and thus, there is a tendency that the oxide is not properly discharged and the weld defects are increased in the weld zone 3.

(Image Capturing Condition)

In order to properly monitor the welded state of the weld zone 3, the camera 4 captures an image of a range from a portion where the steel sheet 1 is in a red heat state to the weld point W of the weld zone 3.

As will be described later, the image processing device 100 determines the geometrical V convergence point $V_0$, the physical abutment point $V_1$, and the weld point W on the basis of the image of the weld zone 3 captured by the camera 4. For that reason, the camera 4 captures an image of the weld point 3 at the resolution with which the image processing device 100 can determine the geometrical V convergence point $V_0$, the physical abutment point $V_1$, and the weld point W.

The image capturing region is required to include a range from a region where red heat of the butt end 1a in the circumferential direction of the steel sheet 1 can be detected by the camera 4 to the weld point W where the butt end 1a is subjected to rolling reduction. The position where the both butt ends 1a are butting each other is deviated in an upstream direction or a downstream direction in the conveyance direction X by a pipe diameter, a film thickness, a heat-input condition, or the like. For that reason, the camera 4 needs to secure an image field of view having 100 mm or more with respect to the conveyance direction X of the steel sheet 1.

From the above-described reason, the camera 4 preferably has the resolution of 60 μm or less when capturing an image of a range having a width of 100 mm or more. The matter that the camera 4 has the resolution of 60 μm or less means that the camera 4 has a resolution narrower than 60 μm (has higher resolution characteristics).

The camera 4 preferably has the resolution of 60 μm or less when capturing an image of a range having a width of 130 mm or more. The camera 4 preferably has a resolution of 60 μm or less when capturing an image of a range having a width of 150 mm or more.

In order to prevent image flow accompanied by press forming of the steel sheet 1 by the roll group and conveying of the steel sheet 1 and obtain a clear image, a shutter speed of the camera 4 is preferably 1/5000 seconds or less. For the same reason as above, 1/10000 seconds or less is more preferable.

In order to properly capture time variation of the welded state, a frame rate (the number of frames captured for one second by a camera) of the camera 4 is preferably 30 fps frames per second (fps) or more.

In order to analyze the welded state by the image processing, it is desirable that the camera 4 clearly captures an image of the welded bead part (a portion represented by a dotted line in FIG. 9A to FIG. 9D) as well as the weld zone 3. The welded bead part refers to a swollen portion formed by flowing out the molten steel to an inner surface and an outer surface of the steel sheet 1 obtained by being press-formed into a tubular shape when both butt ends 1a are butting each other. When the image of welded bead part is captured by the camera 4, a depth of field is preferably set to ±4 mm or more.

In a case where the camera 4 is installed at a position which is 3 m above the weld zone 3, an aperture condition of the camera 4 is preferably set to F8 to F11 in order to satisfy the image capturing condition described above.

The camera 4 preferably adopts a progressive scanning method. The progressive scanning method is an image scanning method for successively scanning images captured at the same timing, and is suitable for capturing moving images.

(Influence of Plasma Irradiation to Capturing an Image of Weld Zone 3 and Avoiding Measures Thereof)

Figure 3:
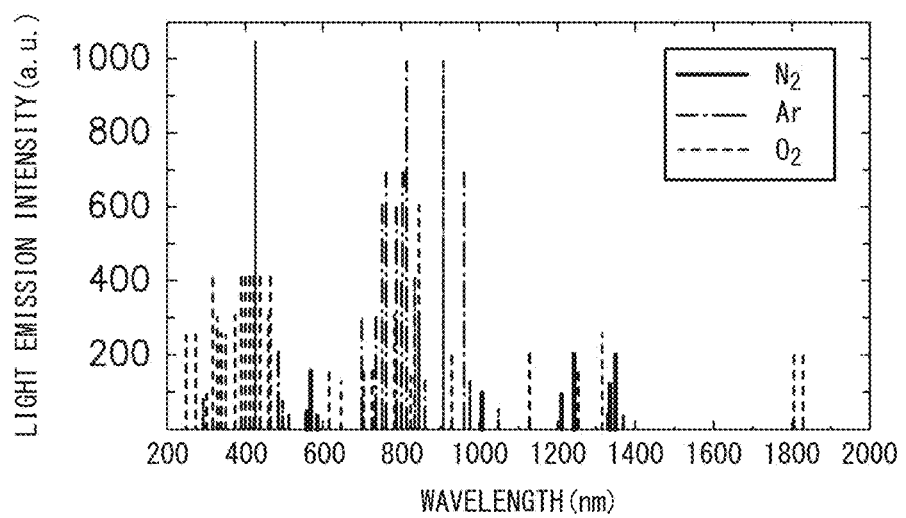
FIG. 3 is a characteristics diagram showing a light emission spectrum of Ar, $N_2$, and $O_2$.

As mentioned above, main components of plasma that the plasma irradiation device 2 irradiates are Ar and $N_2$. It is considered that Ar and $N_2$ emit light by themselves on the basis of each light-emission spectrum (line spectrum). FIG. 3 is a characteristic diagram showing light emission spectrum of Ar, $N_2$, and $O_2$.

Figure 4:
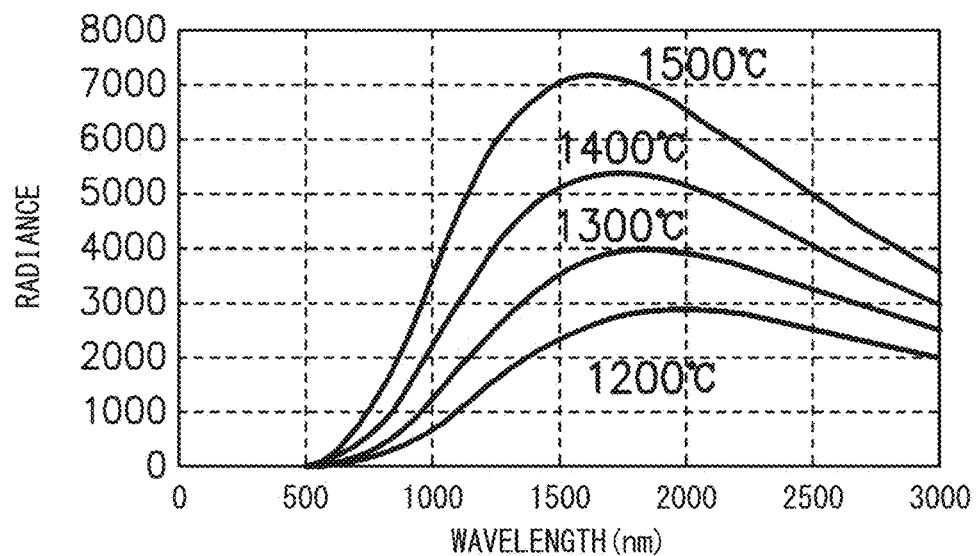
FIG. 4 is a characteristic diagram showing a Planck radiation spectrum.

On the other hand, it is known that light-emission of the molten steel of the butt end 1a of the steel sheet 1 (molten steel has a melting point of 1500° C. or more) is based on a Planck radiation spectrum. FIG. 4 is a characteristic diagram showing Planck radiation spectrum.

Although a wavelength of light emission spectrum of plasma was known, the ratio of Planck radiation from the molten steel to be subjected to image capturing and light emission intensity of plasma was not known. Both of the wavelength of light emission spectrum (or frequency) and the light emission intensity were not known for light emission caused by reaction of plasma with sputter and reaction of plasma with a steel material component.

In Patent Documents 3 and 4, regarding the conventional electric resistance welding, a technique that captures an image of a radiation pattern of a visible region in the weld zone using a color or monochromatic camera formed of CCD image sensors and analyzes a welded state by image processing is disclosed. However, as described above, in a case where an image of the weld zone 3 in the plasma shielded electric resistance welding is captured by the image capturing technique disclosed in Patent Documents 3 and 4, the results of study by inventors of the present application have revealed that a problem that self-luminous light of plasma, light emission caused by reaction of plasma with sputter, and light emission caused by reaction of plasma with a steel material component become an obstacle and analysis of the welded state becomes extremely difficult occurs.

As shown in FIG. 3, since the light emission spectrum of plasma is concentrated on a wavelength region of 400 nm to 800 nm, it is considered that there will be a tendency to suppress an influence caused by self-luminous light of plasma, light emission caused by reaction of plasma with sputter, and light emission caused by reaction of plasma with a steel material component by using an InGaAs image sensor, an InSb image sensor, and the like capable of detecting light having a wavelength of 850 nm or more.

Figure 5:
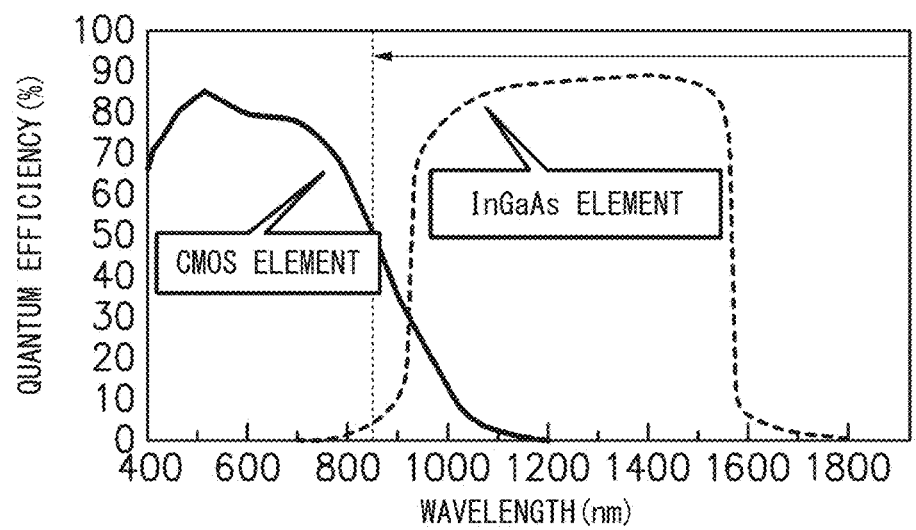
FIG. 5 is a characteristic diagram showing sensitivity characteristics of an InGaAs image sensor and a CMOS image sensor.

As an example, sensitivity characteristic of the InGaAs image sensor is shown in FIG. 5.

However, an image sensor having a large number of pixels that satisfies a condition for the resolution and the field of view described above does not exist among the image sensors capable of detecting light having a wavelength of 850 nm or more. For that reason, a fine slit 8 which accurately represents the welded state cannot be resolved and analysis of the welded state was difficult.

As shown in FIG. 5, a rear surface irradiation CMOS image sensor can detect light having a wavelength of 850 nm or more. Accordingly, the present inventors thought that use of the region where the wavelength is 850 nm or more (region represented by an arrow in FIG. 5) or a portion of the region is effective in order to analyze the welded state in the plasma shielded electric resistance welding which irradiates the weld zone 3 with plasma in order to reduce the weld defects.

Since the CMOS image sensor has low quantum efficiency in the region where the wavelength is 850 nm or more and an amount of Planck radiation is low in the region where the wavelength is 850 nm or more, it was unknown whether a sufficient amount of light is obtained when the image capturing condition described above is satisfied. It is assumed that a sufficient light amount is obtained for a case where an amount of light obtained in a case where a camera is set to the highest sensitivity is 30% or more of the dynamic range. It is preferable that an amount of light which is 50% or more of the dynamic range is obtained. This indicates 75 levels to 128 levels or more in an image represented by 8-bit gradations. In the amount of light equal to or less than the level, a problem that contrast is insufficient, gradation for digitalization becomes coarse, only a discrete value is obtained, or the like occurs in performing a normal image processing.

Accordingly, the condition under which the weld zone 3 (particularly, state of the slit 8) in the plasma shielded electric resistance welding can be resolved is searched by combining the camera 4 using the CMOS image sensor (CMOS camera) and the optical filter 6. The results will be described with reference to FIG. 6A to FIG. 6C.

Figure 6A:
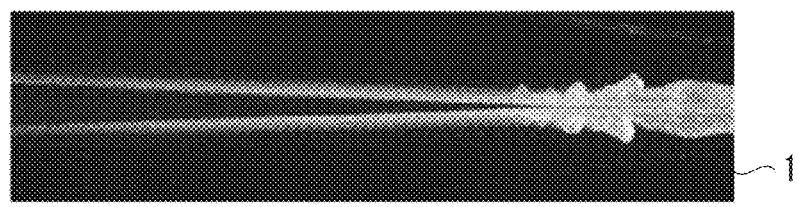
FIG. 6A is a diagram showing an image obtained by capturing the weld zone of the plasma shielded electric resistance welding with a combination of a CMOS camera and an optical filter transmitting only light having a wavelength of 990 nm or more.
Figure 6B:
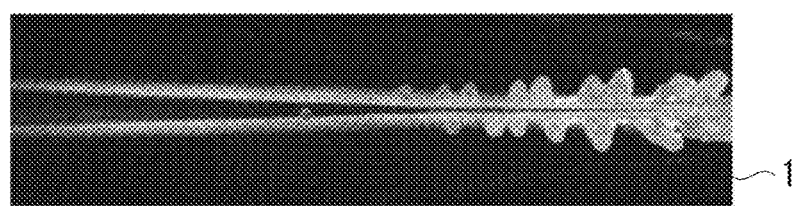
FIG. 6B is a diagram showing an image obtained by capturing the weld zone of the plasma shielded electric resistance welding with a combination of a CMOS camera and an optical filter transmitting only light having a wavelength of 900 nm or more.
Figure 6C:
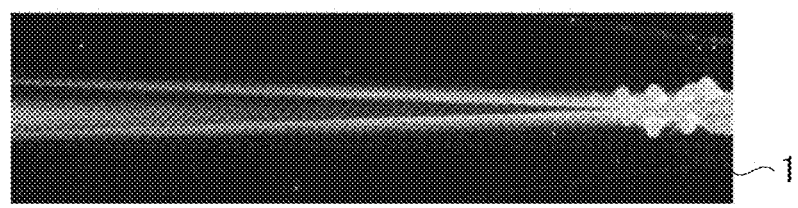
FIG. 6C is a diagram showing an image obtained by capturing the weld zone of the plasma shielded electric resistance welding and a combination of a CMOS camera with an optical filter transmitting only light having a wavelength of 810 nm or more.

In FIGS. 6A to 6C, a direction from the left to the right is the conveyance direction X of the steel sheet 1.

FIG. 6A is an image captured by mounting the optical filter 6, which transmits only light having a wavelength of 990 nm or more, on the camera 4 provided with the CMOS image sensor of which the number of horizontal pixels is 2048. FIG. 6B is an image captured by mounting the optical filter 6, which transmits only light having a wavelength of 900 nm or more, on the camera 4 provided with the CMOS image sensor.

In FIG. 6A and FIG. 6B, the influence, which is given to image capturing of the weld zone 3, by self-luminous light of plasma, light emission caused by reaction of plasma with sputter, and light emission caused by reaction of plasma with a steel material component is suppressed, and the state of the slit 8 is also observed.

On the other hand, FIG. 6C is an image captured by mounting the optical filter 6, which transmits only light having a wavelength of 810 nm or more, on the camera 4 provided with the CMOS image sensor. In FIG. 6C, self-luminous light of plasma, light emission caused by reaction of plasma with sputter, and light emission caused by reaction of plasma with a steel material component have been imaged, which becomes an obstacle for the image processing.

Furthermore, although not shown, in a case where the optical filter 6 transmitting only light having a wavelength of 850 nm or more is mounted on the camera 4 provided with the CMOS image sensor, it is found out that the state of the slit 8 can be observed, similar to the case as shown in FIG. 6A and FIG. 6B.

As described above, inventors of the present application found out that a condition, under which the camera 4 provided with the CMOS image sensor and the optical filter 6 which limits light incident on the camera 4 to the wavelength region of 850 nm or more are combined, is suitable for capturing an image of the weld zone 3.

The optical filter 6 is preferably limit light incident on the camera 4 to the wavelength region of 900 nm or more. Under the condition, it is possible to obtain a sufficient light amount for capturing an image of the radiation pattern from the molten steel using the CMOS image sensor. The influence of plasma is suppressed more on the longer wavelength side and thus, the influence of plasma can be further suppressed than the case of 850 μM under the condition.

The optical filter 6 is preferably limit light incident on the camera 4 to the wavelength region of 990 nm or more.

The optical filter 6 may adopt a configuration in which light incident on the camera 4 is limited only to some of the above-described wavelength regions.

An upper limit of a wavelength of light transmitted through by the optical filter 6 is not defined particularly. However, as shown in FIG. 4, a peak of radiance of Planck radiation exists in the vicinity of 1500 nm and radiance of Planck radiation is reduced in the longer wavelength side. Although not shown in FIG. 4, a significant amount of radiance of Planck radiation is reduced in a region where the wavelength exceeds 5000 nm. For that reason, the upper limit of a wavelength of light transmitted by the optical filter 6 may include, for example, 5000 nm.

In the above description, although a case where the camera 4 including the CMOS image sensor is used as the camera 4, the camera 4 is not limited to the camera 4 including the CMOS image sensor as long as the camera 4 is capable of detecting light having the wavelength of 850 nm or more and the camera 4 satisfies the resolution, field of view, and shutter speed described above.

Figure 7:
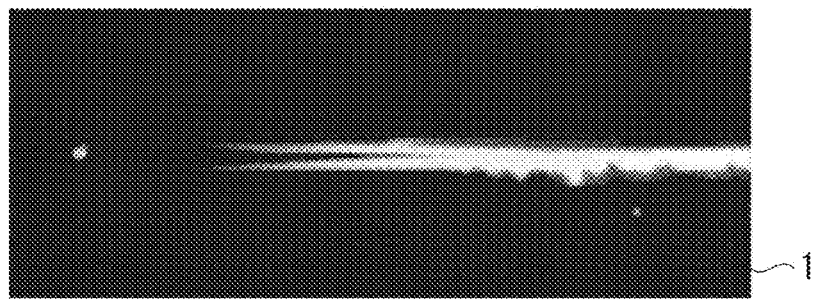
FIG. 7 is a diagram showing an image obtained with capturing the weld zone of the plasma shielded electric resistance welding by the InGaAs image sensor.

As a reference, FIG. 7 shows an image obtained by capturing an image of the weld zone 3 in the plasma shielded electric resistance welding by the InGaAs image sensor. A direction which progresses from the left to the right in FIG. 7 is the conveyance direction X of the steel sheet 1. It is found out that when an image capturing field of view is ensured, the required resolution is not obtained and a detailed welded state of the slit or the like is not able to be recognized. On the other hand, when an element having a larger number of pixels can be manufactured in the future, the In GaAs image sensor, InSb image sensor, or the like can also be applied.

The above-mentioned knowledge becomes obvious for the first time as a result of the earnest research by inventors of the present application.

(Specific Example of Camera 4 and Optical Filter 6)

A lens 5 having a focal length of 300 mm is mounted on the camera 4 using the CMOS image sensor of which the number of horizontal pixels is 2048, the number of vertical pixels is 512, and a frame rate is 200 fps, and the camera 4 is installed downwardly at a position 3 m above the weld zone 3. An optical filter 6 (long wavelength pass filter) having a multilayered film which transmits only light having a wavelength of 900 nm or more is mounted on a front surface of the lens 5 of the camera 4. It is adjusted such that a field of view is about 130 mm for the conveyance direction X of the steel sheet 1 when capturing an image. The shutter speed of the camera 4 is set to $1/10000$ seconds and a lens aperture of the camera 4 is set to F8.

Since only light having a wavelength of 900 nm or more is allowed to be transmitted through in a state where the optical filter 6 is mounted, it is unable to obtain an image in which the target to be subjected to image capturing can be determined, for example, in a case where a target to be subjected to image capturing is irradiated by an LED or a fluorescent lamp. For that reason, the field of view of the camera 4 is preferably adjusted in a state where the optical filter 6 is removed.

Even in a state where the optical filter 6 is mounted, a scale (a ruler with calibrations which represent dimensions or the like) may be irradiated by a light source which generates light having a wavelength of 900 nm or more. As an example of such a light source, a halogen light source may be included. In this case, even in a state where the optical filter 6 is mounted, the field of view of the camera 4 can be adjusted.

(Specific Example of the Image Processing Device 100)

The image processing device 100 subjects the image of the weld zone 3 sent from the camera 4 to image processing so as to analyze behaviors of three points of the geometrical V convergence point $V_0$, the physical abutment point $V_1$, and the weld point W, the state of the slit 8, and the state of the V-shaped convergence region.

A method for calculating the geometrical V convergence point $V_0$, the physical abutment point $V_1$, and the weld point W using an image processing device 100 will be described with reference to FIG. 8, and FIG. 9A to FIG. 9D.

Figure 8:
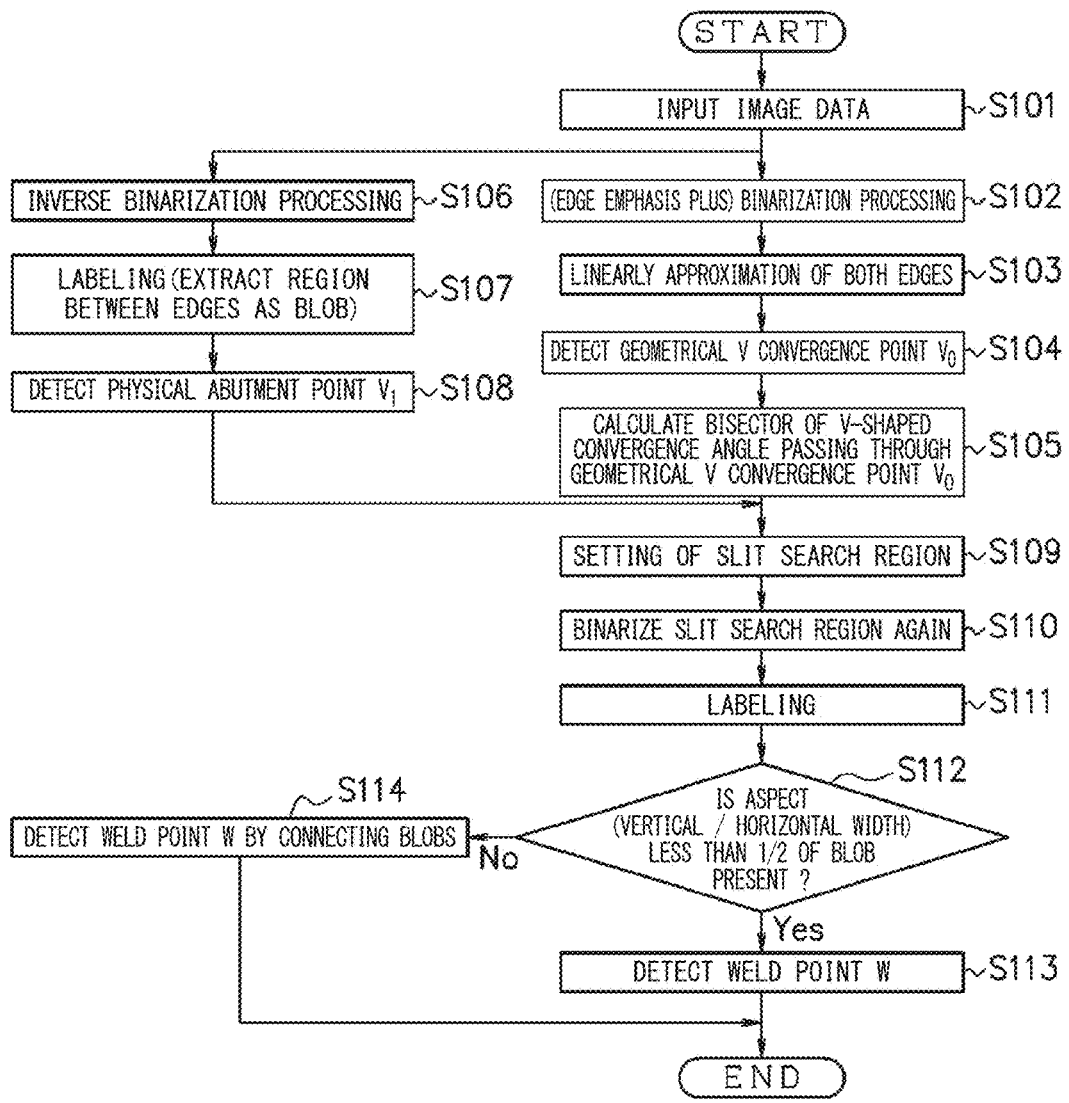
FIG. 8 is a flowchart showing an example of a process for analyzing the welded state of the weld zone using an image processing device.

FIG. 8 is a flowchart showing an example of a process for analyzing the welded state of the weld zone 3 using the image processing device 100.

Figure 9A:
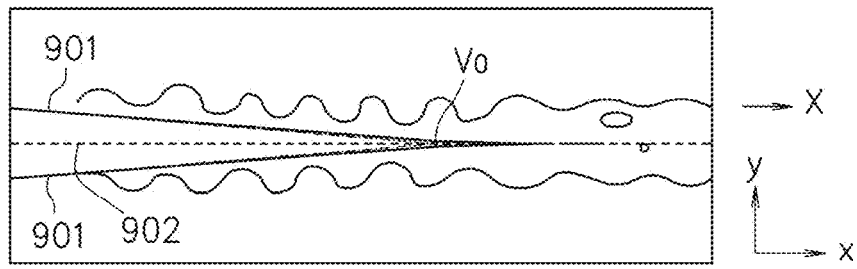
FIG. 9A is a schematic diagram showing a method for linearly approximating a butt end in an image binarized by the image processing device.
Figure 9B:
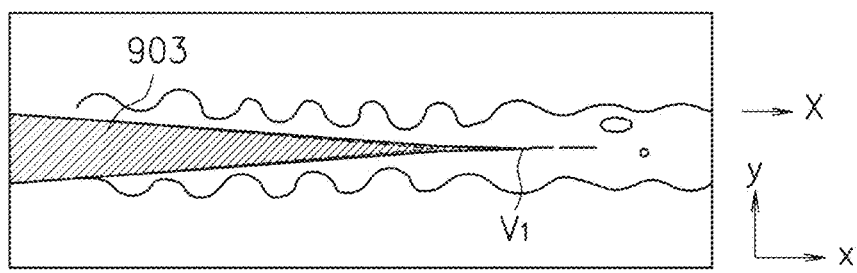
FIG. 9B is a schematic diagram showing a method for extracting a blob of a V-shaped convergence region by the image processing device.
Figure 9C:
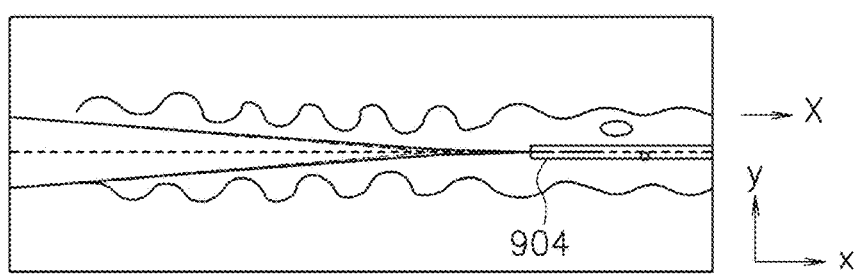
FIG. 9C is a schematic diagram showing a method for setting a slit search region by the image processing device.
Figure 9D:
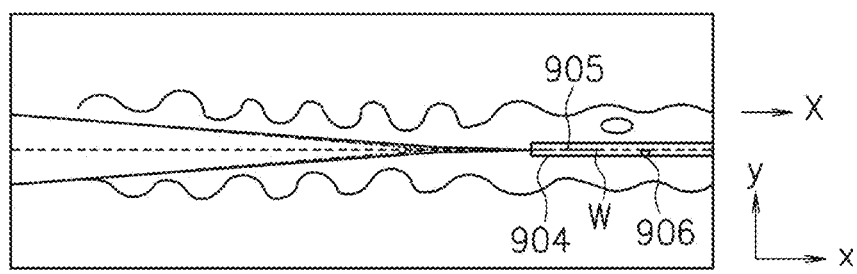
FIG. 9D is a schematic diagram showing a method for detecting a weld point W by the image processing device.

FIG. 9A is a schematic diagram showing a method for linearly approximating the butt end 1a in the image subjected to binarization by an image processing device 100. FIG. 9B is a schematic diagram showing a method for extracting blobs of the V-shaped convergence region by the image processing device 100. FIG. 9C is a schematic diagram showing a method for setting a slit search region by the image processing device 100. FIG. 9D is a schematic diagram showing a method for detecting the weld point W by the image processing device 100.

The image processing device 100 repeatedly executes the image processing shown in FIG. 8 each time when the image data is sent from the camera 4.

In Step S101, the image processing device 100 receives the image data sent from the camera 4.

In Step S102, the image processing device 100 binarizes the image received in Step S101. In Step S102, the image processing device 100 performs edge emphasis processing on the image received in Step S101 as needed.

In Step S103, the image processing device 100 linearly approximates the butt end 1a of the steel sheet 1 in the image subjected to binarization in Step S102. A schematic diagram of the image of the butt end 1a which is subjected to linear approximation is shown in FIG. 9A.

In a case where the welded state is Type 1, Type 2, and the transition region, the butt end 1a is linearly approximated by the method described above.

On the other hand, in a case where the welded state is Type 2' and the excessive heat-input, linear approximation of the butt end 1a is performed in an upstream part of the conveyance direction X of the steel sheet 1 than a position where a second-stage convergence is started.

In Step S104, the image processing device 100 regards an intersection point of a butt end 901 which is subjected to linear approximation in Step S103 as the geometrical V convergence point $V_0$.

In Step S105, the image processing device 100 calculates a bisector 902 of an angle formed by a pair of the butt ends 901 which are subjected to linear approximation and the geometrical V convergence point $V_0$ (V-shaped convergence angle).

In Step S106, the image processing device 100 performs inverse binarization on the image received in Step S101 in parallel with Step S102 to Step S105.

In Step S107, the image processing device 100 performs labeling processing, which allocates a label to each blob, on the image which is subjected to the inverse binarization in Step S106. As shown in FIG. 9B, the image processing device 100 extracts a blob, which matches a predetermined condition, as a blob 903 of the V-shaped convergence region formed by both butt ends 1a of the steel sheet 1.

The blob is a region to which the same label is allocated.

The predetermined condition includes, for example, a condition that the blob contacts only the left end of the image without being contacted with the right end of the image, an area is 50 mm$^2$ or more, and a value (aspect ratio) obtained by dividing a longitudinal length of the blob by a lateral length of the blob is 0.2 or less.

In Step S108, the image processing device 100 regards a point at the lowermost stream of the blob 903 of the V-shaped convergence region extracted in Step S107 as the physical abutment point $V_1$.

In Step S109, the image processing device 100 sets a slit search region 904 in the image which is subjected to binarization in Step S102. A portion which is observed as one line and in which the both butt ends 1a of the steel sheet 1 are butting each other is called a weld line. In the present embodiment, it is assumed that the weld line is located on the bisector 902 of the V-shaped convergence angle obtained in Step S105.

As shown in FIG. 9C, the slit search region 904 is regarded as a rectangular region surrounding the bisector 902 of the V-shaped convergence angle. Specifically, the physical abutment point $V_1$ is regarded as an upstream end of the slit search region 904 and a downstream end of the image is regarded as a downstream end of the slit search region 904.

As shown in FIG. 9C, the slit search region 904 is a region having a predetermined width (for example, 2 mm) in each of the positive direction and negative direction of the y-axis from the bisector 902 of the V-shaped convergence angle.

In Step S110, the image processing device 100 binarizes the slit search region 904 which is set in Step S109 again.

In Step S111, the image processing device 100 performs the labeling processing, which allocates a label to each blob, on the binarized image of the slit search region 904 obtained in Step S110.

In Step S112, the image processing device 100 calculates an aspect ratio of each blob which is subjected to the labeling processing in Step S111 and determines whether or not the aspect ratio is less than 1/2.

As a result of the determination, in a case where the blob having the aspect ratio which is less than 1/2 exists, the process proceeds to Step S113 and the point at the lowermost stream of the blob located at the lowermost stream in the conveyance direction X of the steel sheet 1, among the blobs having the aspect ratio which is less than 1/2, as the weld point W.

In a case of FIG. 9D, since the aspect ratio is 1/2 and a blob located at the lowermost stream for the conveyance direction X of the steel sheet 1 is a blob 905, the point, which is at the lowermost stream in the conveyance direction X of the steel sheet 1, of the blob 905 is set as the weld point W.

On the other hand, in a case where a blob having the aspect ratio which is less than 1/2 does not exist on the image, the process proceeds to Step S114, and after connecting the blob located on the bisector 902 of the V-shaped convergence angel, a point at the lowermost stream in the conveyance direction X of the steel sheet 1 in the connected blob is set as the weld point W.

In this manner, the position of the weld point W is set on the basis of the aspect ratio of the blob and thus, it becomes possible to remove a blob 906 even in a case where the blob 906 due to noise is present within the slit search region 904.

As described above, according to the welded state monitoring system relating to the present embodiment, it is possible to analyze the welded state on the basis of an image obtained by capturing the weld zone 3 while suppressing an influence by plasma irradiation by capturing the image of the weld zone 3 from above using the camera 4, after being limited such that only light having a wavelength of 900 nm or more is incident on the camera 4.

Although description has been made mainly on the image processing by the image processing device 100, for example, the geometrical V convergence point $V_0$, the physical abutment point $V_1$, and the weld point W may be displayed on a monitor by being superposed on the image captured by the camera 4 on the basis of the result of the image processing.

When a distance between $V_1$ and $V_0$ is, for example, a setting value or less, the amount of heat-input may be set so as to be increased on the basis of the result of the image processing. In such a case, it is not necessary to detect the position of the weld point W. When a distance between the weld point W and the squeeze roll 7 becomes the setting value or more, from the position of the detected weld point W, a control may be performed so as to lower the amount of heat-input.

Second Embodiment

In the second embodiment, an example in which plasma irradiation positions are simultaneously detected, in addition to the analysis of the welded state explained in the first embodiment.

Since the weld zone 3 is sandwiched between top rollers, the butt end 1a of the steel sheet 1 approximates at a narrow angle of several degrees or less, or the like, spatial restriction is imposed on the plasma irradiation device 2. For that reason, since an effective diameter of plasma is limited, a range capable of being irradiated with plasma is limited, and when the plasma irradiation position to the weld zone 3 is deviated, a desired quality of welding cannot be obtained.

A relationship between the plasma irradiation position and the defect occurrence ratio will be described with reference to FIG. 10.

Figure 10:
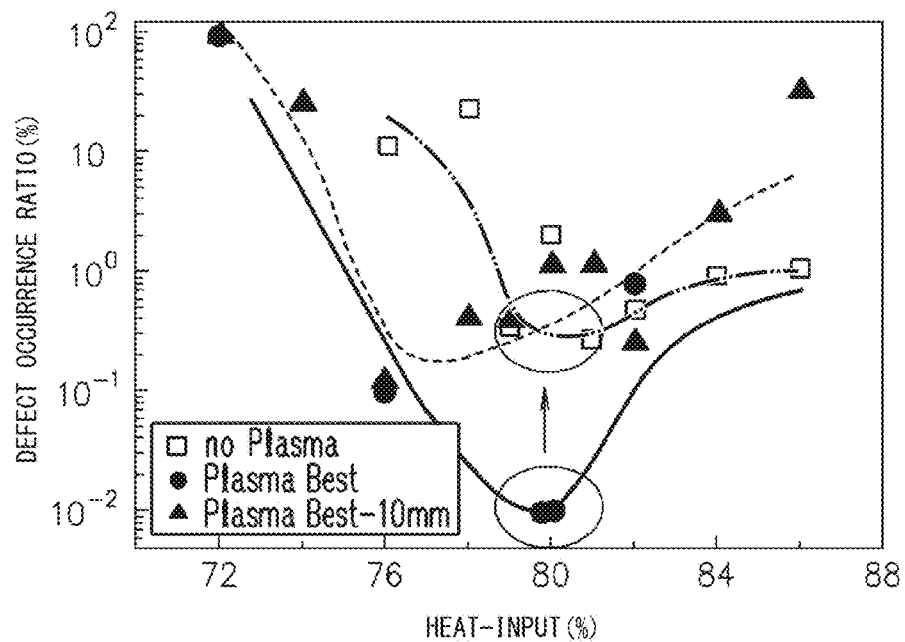
FIG. 10 is a diagram showing a relationship between an amount of heat-input and a defect occurrence ratio in welding.

FIG. 10 is a diagram in which a relationship between the amount of heat-input and the defect occurrence ratio of welding in the plasma shielded electric resistance welding is shown for a case where plasma irradiation is not performed (white square in the figure), a case where a plasma irradiation position is appropriate (black circle in the figure), and a case where the plasma irradiation position is deviated from an appropriate position to the conveyance direction X of the steel sheet 1 by 10 mm (black triangle in the figure).

The horizontal axis of FIG. 10 represents the amount of heat-input and is expressed as a ratio of an amount of heat-input to a reference amount of heat-input during operation.

The vertical axis in FIG. 10 represents an occurrence ratio of weld defects and is expressed by a ratio of a defect occurrence area to a total area of the welded portion.

A solid line in FIG. 10 is an approximate curve regarding the relationship between the amount of heat-input and the occurrence ratio of weld defects in a case where the plasma irradiation position is appropriate. A dotted line in FIG. 10 is an approximate curve regarding the relationship between the amount of heat-input and the occurrence ratio of weld defects in a case where the plasma irradiation position is deviated from an appropriate position to an upstream direction of the conveyance direction X of the steel sheet 1 by 10 mm. A dashed line in FIG. 10 is an approximate curve regarding the relationship between the amount of heat-input and the occurrence ratio of weld defects in a case where the plasma irradiation is not performed.

FIG. 10 shows matters that in a case where the amount of heat-input is 80%, the plasma irradiation position is deviated from an appropriate position to the upstream direction of the conveyance direction X of the steel sheet 1 by 10 mm and thus the occurrence ratio of weld defects is increased by several ten times (portion surrounded by a circle in FIG. 10)

Furthermore, FIG. 10 shows matters that in a case where the amount of heat-input is 80%, the plasma irradiation position is deviated from an appropriate position to the upstream direction of the conveyance direction X of the steel sheet 1 by 10 mm and thus the occurrence ratio of weld defects is substantially the same as the case where the plasma irradiation is not performed.

Conventionally, the plasma irradiation device 2 estimates a position of the geometrical V convergence point $V_0$ in advance in a state where only press forming is performed without performing welding and determines the plasma irradiation position on the basis of the estimated position of the geometrical V convergence point $V_0$. However, the position of the geometrical V convergence point $V_0$ may be deviated by 10 mm or more in a case where the welding is performed and a case where the welding is not performed. The position of the geometrical V convergence point $V_0$ varies even by the press forming state due to the amount of heat-input and the roll group. For that reason, there was a problem that the plasma irradiation position is deviated from the appropriate position in the conventional plasma irradiation position determination method and the quality of welding is deteriorated.

In this manner, it is required to detect whether or not the plasma irradiation position is appropriate in real time.

Figure 11:
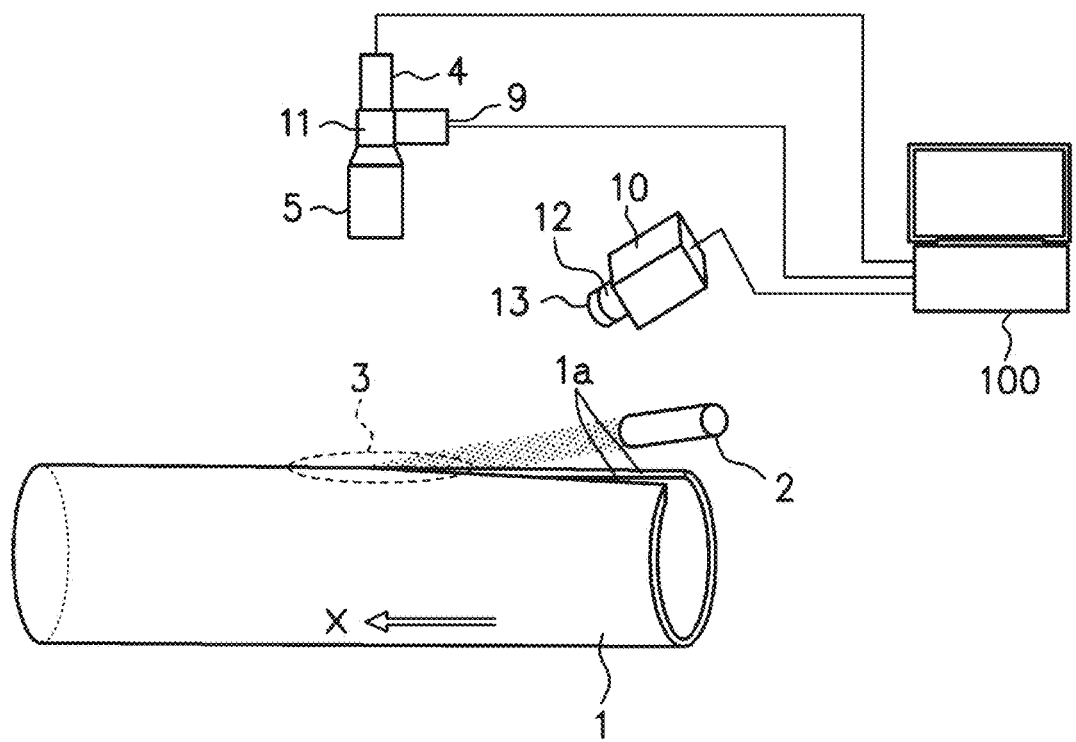
FIG. 11 is a diagram schematically showing a configuration of a welded state monitoring system in plasma shielded electric resistance welding according to a second embodiment.

FIG. 11 is a diagram schematically showing a configuration of a welded state monitoring system in plasma shielded electric resistance welding according to a second embodiment. The same constitutional elements as those of the first embodiment are assigned the same reference numerals, and descriptions thereof will not be repeated.

In the second embodiment, a second camera 9 and a third camera 10 are installed in addition to the camera 4 (hereinafter, referred to as a first camera in the present embodiment).

The second camera 9 is installed in order to detect the plasma irradiation position in a direction (width direction of the steel sheet 1) orthogonal to the conveyance direction X of the steel sheet 1, as will be described in detail in the following.

The first camera 4 and the second camera 9 share the lens 5 and a branch unit 11 is assembled between the first camera 4, the second camera 9, and the lens 5. The branch unit 11 includes a multilayered film which separates incident light into light having a wavelength of 900 nm or more and light having a wavelength of 500 nm or less.

That is, only light having a wavelength of 900 nm or more is incident on the first camera 4 and only light having a wavelength of 500 nm or less is incident on the second camera 9 in a state where the field of view of the first camera 4 matches with that of the second camera 9.

As described above, the branch unit 11 preferably limits the wavelength of light incident on the second camera 9 to 500 nm or less. The second camera 9 is a camera not for capturing an image of Planck radiation but for capturing an image of plasma in the butt end 1a of the steel sheet 1. For that reason, the branch unit 11 can limit incidence of light due to Planck radiation on the second camera 9 by limiting the wavelength of light incident on the second camera 9 to 500 nm or less.

The branch unit 11 preferably limits the wavelength of light incident on the second camera 9 to 450 nm or less. As shown in FIG. 3, light-emission spectra of Ar and $N_2$ have light intensity also in the region having a wavelength of 450 nm or less. On the other hand, as shown in FIG. 4, radiance of Planck radiation is further reduced than a case where the wavelength is 500 nm and approaches zero, in the region having a wavelength of 450 nm or less. For that reason, an image of plasma light-emission can be captured by the second camera 9 in a state where influence by Planck radiation is reduced by limiting the wavelength of light incident on the second camera 9 to 450 nm or less by the branch unit 11.

The branch unit 11 may limit the wavelength of light incident on the second camera 9 to a portion of the wavelength region of 500 nm or less to be a wavelength region having wavelength of 400 nm to 500 nm or a wavelength region having wavelength of 400 nm to 450 nm.

In the second embodiment, the branch unit 11 corresponds to a first wavelength region limitation device and a second wavelength region limitation device referred to in the present invention.

The range of the wavelength of light incident on the first camera 4 limited by the branch unit 11 is the same as the range of the wavelength of light incident on the camera 4 limited by the optical filter 6 in the first embodiment.

In order to match the fields of view of the first camera 4 and the second camera 9, at least one camera of the first camera 4 and the second camera 9 has an adjustment mechanism having a total of four axes of an optical axis and three axes, which are a vertical surface to the optical axis, that translate and rotate centering on the optical axis. When making the fields of view of the first camera 4 and the second camera 9 match with each other, a calibration plate that depicts a rectangle representing a target field of view or a scale which is orthogonal is installed on a measurement target surface, an image of the calibration plate and the scale is captured using the first camera 4 and the second camera 9, and the fields of view of the first camera 4 and the second camera 9 are adjusted such that respective captured images match with each other. By superposing the image captured by the first camera 4 with the image captured by the second camera 9, the fields of view of the first camera 4 and the second camera 9 can be adjusted.

The third camera 10 is installed in order to detect the plasma irradiation position in the conveyance direction X of the steel sheet 1, as will be described in detail in the following.

An optical filter 13 (short wavelength pass filter) is mounted, for example, on the front surface of a lens 12 of a third camera 10, The optical filter 13 preferably limits the wavelength of light incident on the third camera 10 to 500 nm or less. The third camera 10 is a camera not for capturing an image of Planck radiation but for capturing an image of plasma in the butt end 1a of the steel sheet 1, similar to the second camera 9. For that reason, the optical filter 13 can limit incidence of light due to Planck radiation on the third camera 10 by limiting the wavelength of light incident on the third camera 10 to the range described above.

The optical filter 13 preferably limits the wavelength of light incident on the third camera 10 to 450 nm or less. As shown in FIG. 3, light-emission spectra of Ar and $N_2$ have light intensity also in the region having a wavelength of 450 nm or less. On the other hand, as shown in FIG. 4, radiance of Planck radiation is further reduced than a case where the wavelength is 500 nm and approaches zero, in the region having a wavelength of 450 nm or less. For that reason, an image of plasma light-emission can be captured by the third camera 10 in a state where influence by Planck radiation is further reduced by limiting the wavelength of light incident on the third camera 10 to 450 nm or less by the optical filter 13.

The optical filter 13 may limit the wavelength of light incident on the third camera 10 to a portion of the wavelength region of 500 nm or less to be a wavelength region having wavelength of 400 nm to 500 nm or a wavelength region having wavelength of 400 nm to 450 nm.

In the second embodiment, the optical filter 13 corresponds to a third wavelength region limitation device in the present invention.

An arrangement of the third camera 10 will be described with reference to FIG. 12A and FIG. 12B.

Figure 12A:
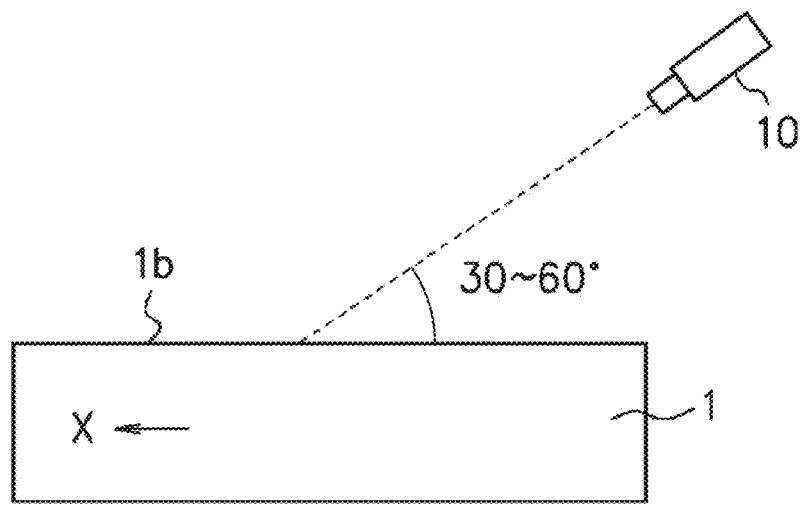
FIG. 12A is a diagram showing an arrangement of a third camera viewed from a lateral side of a steel sheet.

FIG. 12A is a diagram showing an arrangement of the third camera 10 viewed from a lateral side of the steel sheet 1. FIG. 12B is a diagram showing the arrangement of the third camera 10 viewed from above the steel sheet 1.

The third camera 10 captures an image of the weld zone 3 from a slanted direction of any of the left and right of the conveyance direction X at a location above the upstream of the conveyance direction X of the steel sheet 1 (which is already press formed into a steel pipe shape).

As shown in FIG. 12A, the third camera 10 is preferably installed at a range of about 30° to about 60° above an upper edge 1b of the steel sheet 1 when viewed from the lateral side of the steel sheet 1.

Figure 12B:
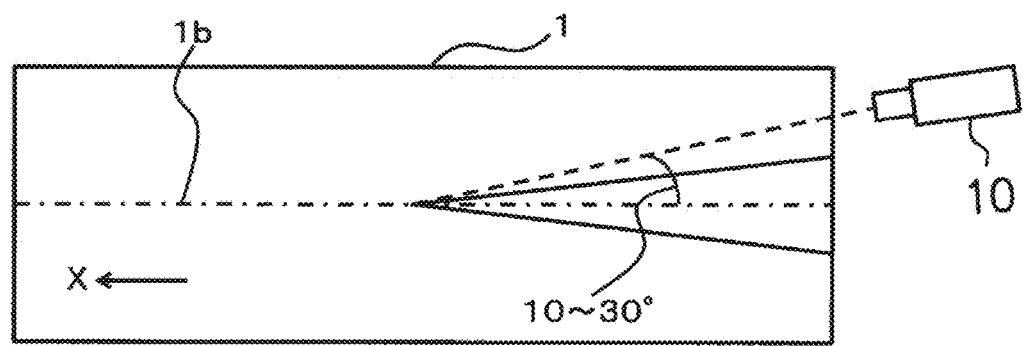
FIG. 12B is a diagram showing an arrangement of the third camera viewed from above the steel sheet.

As shown in FIG. 12B, the third camera 10 is preferably installed at a range of about 10° to about 30° in the width direction (up-and-down direction of the conveyance direction X of the steel sheet 1 in FIG. 12B) with respect to the upper edge 1b when viewed from above the steel sheet 1 (which is already press formed into a steel pipe shape).

The third camera 10 is installed at the position described above and then adjusts the position of the third camera 10 such that both the entirety of plasma and the weld zone 3 are imaged using the third camera 10. After the installation position of the third camera 10 is determined, an image capturing range of the third camera 10 is adjusted such that positions of the weld lines correspond to each other in the image captured by the third camera 10 and the image captured by the first camera 4.

As the second camera 9 and third camera 10, a mochromatic camera provided with a CMOS image sensor can be used, for example, similar to the first camera 4.

Plasma exhibits movement specific to plasma, which is called plasma vibration. For that reason, in a case where exposure time of the second camera 9 and the third camera 10 is reduced when capturing an image of plasma, there is a possibility that the image of plasma cannot be appropriately captured. For that reason, the exposure time of the second camera 9 and the third camera 10 is made long (for example, 1/40 seconds) to capture an image of plasma in the present embodiment.

Since the light-emission amount of plasma is very large, it is preferable that a dimmer filter is mounted on the second camera 9 and the third camera 10.

(Detection of Plasma Irradiation Position in the Width Direction of Steel Sheet 1)

A method for detecting the plasma irradiation position in the width direction of the steel sheet 1 using the image processing device 100 will be described with reference to FIG. 13 and FIG. 14A to FIG. 14E.

Figure 13:
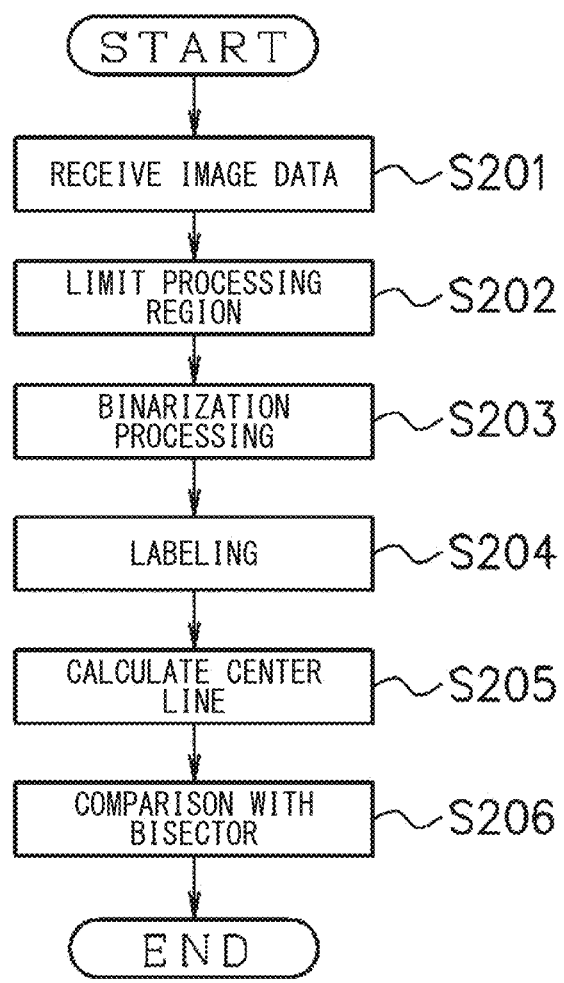
FIG. 13 is a flowchart showing an example of a process for detecting a plasma irradiation position in a width direction of the steel sheet using the image processing device.
Figure 14A:
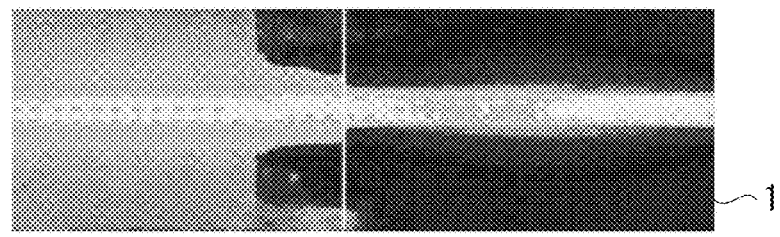
FIG. 14A is a diagram showing an image obtained by capturing the weld zone of the plasma shielded electric resistance welding by the second camera.
Figure 14B:
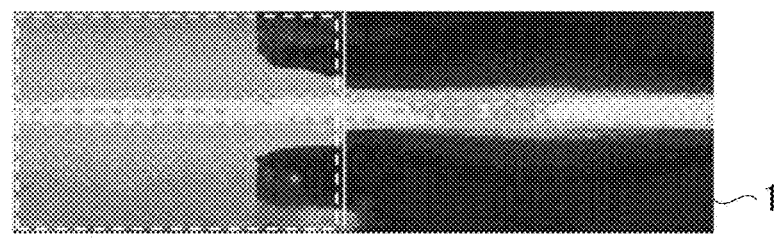
FIG. 14B is a diagram showing extraction of an image processing region by the image processing device.

FIG. 13 is a flowchart showing an example of a process for detecting a plasma irradiation position in a width direction of the steel sheet 1 using the image processing device 100. FIG. 14A is a diagram showing an image obtained by capturing the weld zone 3 of the steel sheet 1 by the second camera. FIG. 14B is a diagram showing extraction of an image processing region by the image processing device 100 in order to detect the plasma irradiation position in the width direction of the steel sheet 1.

Figure 14C:
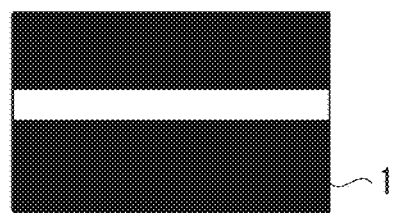
FIG. 14C is a schematic diagram showing binarization of plasma images by the image processing device.
Figure 14D:
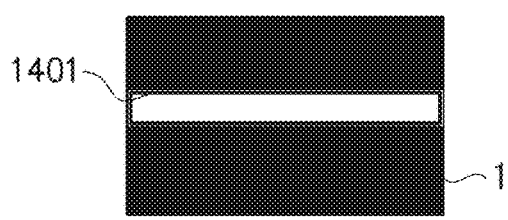
FIG. 14D is a diagram showing detection of plasma blobs by the image processing device.
Figure 14E:
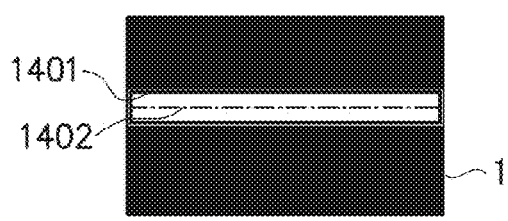
FIG. 14E is a diagram showing calculation of a center line of the plasma blobs by the image processing device.

FIG. 14C is a schematic diagram showing binarization of an image of plasma by the image processing device 100 in order to detect the plasma irradiation position in a width direction of the steel sheet 1. FIG. 14D is a diagram showing detection of plasma blobs by the image processing device 100 in order to detect the plasma irradiation position in the width direction of the steel sheet 1. FIG. 14E is a diagram showing a center line of the blobs of plasma by the image processing device 100 in order to detect the plasma irradiation position in the width direction of the steel sheet 1.

In the following description, a case where a frame rate of the first camera 4 is 200 fps and a frame rate of the second camera 9 is 40 fps will be descried. In this case, the first camera 4 captures five frames while the second camera 9 captures one frame.

In the descriptions of FIG. 13, an image captured by the first camera 4 is referred to as a weld zone image and an image captured by the second camera 9 is referred to as a plasma image.

First, in Step S201, the image processing device 100 receives plasma image data (see FIG. 14A) sent from the second camera 9.

Next, in Step S202, the image processing device 100 limits a region to be subjected to image processing (processing region) for the plasma image received in Step S201.

Only light having a wavelength of 500 nm or less is incident on the second camera 9 by the multilayered film provided in the branch unit 11. For that reason, light caused by reaction of plasma with sputter and light caused by reaction of sputter with a steel material component are incident on the second camera 9, in addition to light caused by plasma.

In the image obtained by capturing the weld zone 3, in a region where in addition to light caused by plasma, light caused by reaction of plasma with sputter and light caused by reaction of sputter with a steel material component are mixed, it is difficult to appropriately subject the plasma image to the image processing.

In the image where the weld zone 3 is captured, in addition to light caused by plasma, light caused by reaction of plasma with sputter and reaction of sputter with a steel material component are mixed in a region located at downstream of the physical abutment point $V_1$ in the downstream of the conveyance direction X of the steel sheet 1, as described above.

On the other hand, the reaction of plasma with sputter and reaction of plasma with a steel material component do not occur in a region located at upstream of the physical abutment point $V_1$ in the conveyance direction X of the steel sheet 1.

For that reason, it is possible to appropriately subject the plasma image to the image processing in the region located at upstream of the physical abutment point $V_1$ of the conveyance direction X of the steel sheet 1 in the image obtained by capturing the weld zone 3.

From the above-described reason, in Step S202, the image processing device 100 sets the region located at upstream of the physical abutment point $V_1$ in the conveyance direction X of the steel sheet 1 as the processing region in the image obtained by capturing the weld zone 3.

Specifically, in Step S202, the image processing device 100 sets a region surrounded by a white dotted line in FIG. 14B as the processing region.

The image subjected to the image processing in Step S202 is originally an image captured by the second camera 9. For that reason, five frames of the weld zone image are captured by the first camera 4 until a frame one before the image is captured after the frame is captured. For each of the weld zone images, the physical abutment point $V_1$ is detected in Step S108 shown in FIG. 8.

In Step S202, the image processing device 100 calculates an average position of the physical abutment point $V_1$ of the five frames and sets upstream of the average position in the conveyance direction X of the steel sheet 1 as the processing region.

In Step S203, the image processing device 100 binarizes the processing region which is set in Step S202 as shown in FIG. 14C.

In Step S204, the image processing device 100 performs the labeling processing which allocates a label to each blob for the processing region which is subjected to binarization in Step S203 and extracts the blob which matches with a predetermined condition, as a blob 1401 as shown in FIG. 14D. The predetermined condition includes a condition that each blob contacts both ends of the processing region and has an area of 1000 mm$^2$, or the like.

In Step S205, the image processing device 100 calculates a center line 1402 of the width direction of the steel sheet 1 (hereinafter, simply referred to as a center line) for the blob 1401 extracted in Step S204 as shown in FIG. 14E. The center line 1402 is extended toward the conveyance direction X of the steel sheet 1.

Next, in Step S206, the image processing device 100 obtains deviation and obliqueness of the center line 1402 of the blob 1401 of plasma to the bisector 902 in the width direction (that is, the weld line) of the V-shaped convergence angle obtained in Step 105 of FIG. 8. That is, the plasma irradiation position in the width direction of the steel sheet 1 is detected as a relative position with the weld zone 3 of which image is captured by the first camera 4. In a case where the center line 1402 of the blob 1401 of plasma is greatly deviated with respect to the bisector 902 of the V-shaped convergence angle or in a case where the center line 1402 of the blob 1401 of plasma is greatly oblique with respect to the bisector 902 of the V-shaped convergence angle, the plasma irradiation position with respect to the width direction of the steel sheet 1 is not proper.

Although description has been made mainly on the image processing by the image processing device 100, for example, the image of plasma captured by the second camera 9 may be displayed on a monitor by being superposed on the image of the weld zone 3 captured by the first camera 4. In this case, the blob 1401 of plasma, the center line 1402, the physical abutment point $V_1$ and the like may be superposed with each other. With this, it is possible to express numerically and sensuously the deviation of the plasma irradiation position from the width direction of the steel sheet 1 so as to facilitate adjustment of the plasma irradiation position manually.

In a case where the center line 1402 of the blob 1401 of plasma is deviated from the bisector 902 of the V-shaped convergence angle by a predetermined threshold or more or in a case where the center line 1402 of the blob 1401 of plasma is oblique with respect to the bisector 902 of the V-shaped convergence angle by a predetermined threshold or more, it may be configured such that the plasma irradiation position is automatically adjusted so as to match the bisector 902 of the V-shaped convergence angle with the center line 1402 of the blob 1401 of plasma.

(Detection of the Plasma Irradiation Position in the Conveyance Direction X of Steel Sheet 1)

The image processing device 100 subjects an image of the weld zone 3 of the steel sheet 1 sent from the third camera 10 to image processing and detects the plasma irradiation position in the conveyance direction X of steel sheet 1.

An image captured by the third camera 10 will be described with reference to FIG. 15A and FIG. 15B.

Figure 15A:
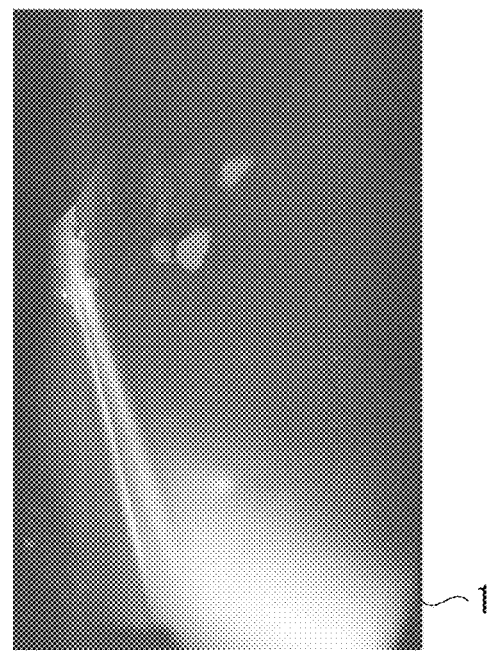
FIG. 15A is a diagram showing an image obtained by capturing the weld zone of the plasma shielded electric resistance welding by the third camera.
Figure 15B:
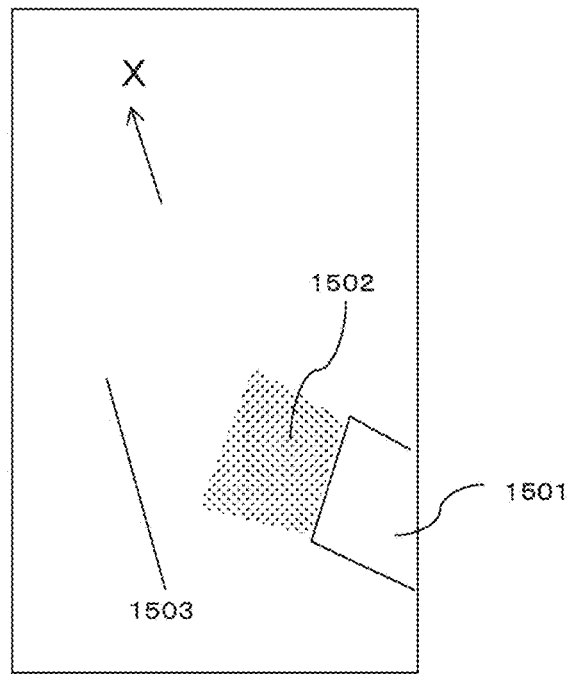
FIG. 15B is a diagram showing a positional relationship between a plasma torch, plasma gas, and a weld line in FIG. 15A.

FIG. 15A is a diagram showing an image obtained by capturing the weld zone 3 by the third camera 10. FIG. 15B is a diagram showing a positional relationship between a plasma torch 1501, plasma gas 1502, and a bisector 1503 of the V-shaped convergence angle in FIG. 15A.

The third camera 10 is located at upstream in the conveyance direction of the steel sheet 1 and captures an image of the weld zone 3 from above of the steel sheet 1 and from an oblique direction any of the left and right of in the conveyance direction X of the steel sheet 1. For that reason, as shown in FIG. 15A and FIG. 15B, a direction of the image captured by the third camera 10 is different from a direction of the image captured by the first camera 4 and the second camera 9.

The image shown in FIG. 15A is an image captured in a state where the optical filter 13 is not mounted.

In detection of the plasma irradiation position in the conveyance direction X of the steel sheet 1 using the image processing device 100, the image of the steel sheet 1 in which a marker is installed is captured by the first camera 4 and the third camera 10 and then the image captured by the first camera 4 and the image captured by the third camera 10 are associated with each other in advance.

A method for detecting the plasma irradiation position in the conveyance direction X of the steel sheet 1 will be described with reference to FIG. 16 and FIGS. 17A to 17C.

Figure 16:
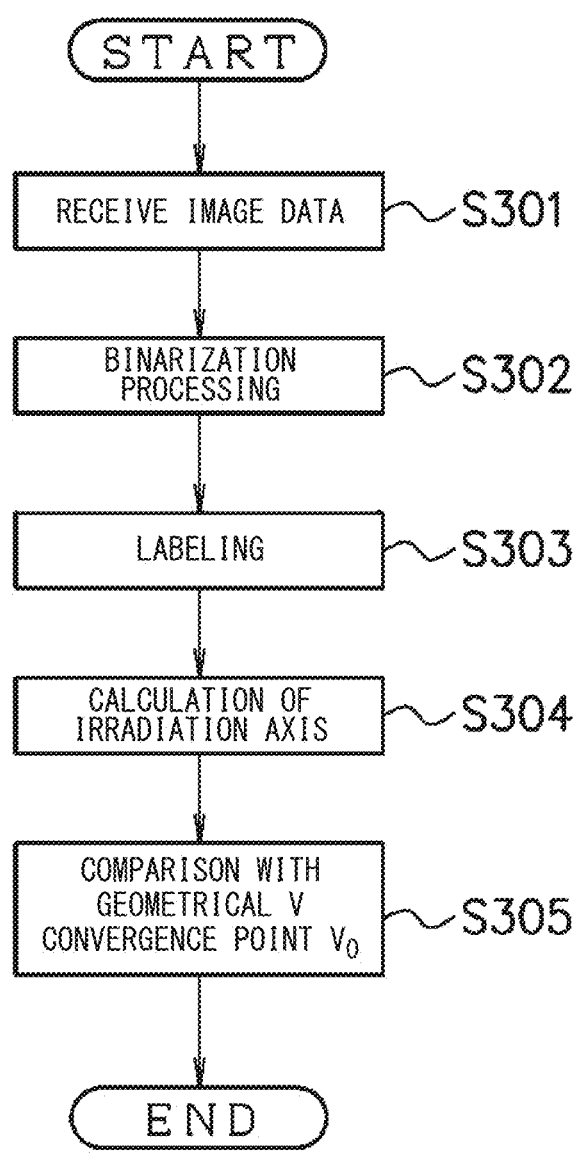
FIG. 16 is a flowchart showing an example of a process for detecting a plasma irradiation position in a conveyance direction of the steel sheet using the image processing device.
Figure 17A:
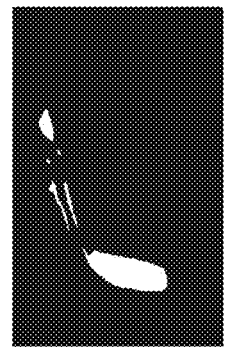
FIG. 17A is a schematic diagram showing binarization of the plasma images when detecting a plasma irradiation position in the conveyance direction of the steel sheet using the image processing device.

FIG. 16 is a flowchart showing an example of a process for detecting the plasma irradiation position in the conveyance direction X of the steel sheet 1 using the image processing device 100. FIG. 17A is a schematic diagram showing binarization of the plasma image by the image processing device 100 in order to detect the plasma irradiation position in the conveyance direction X of the steel sheet 1.

Figure 17B:
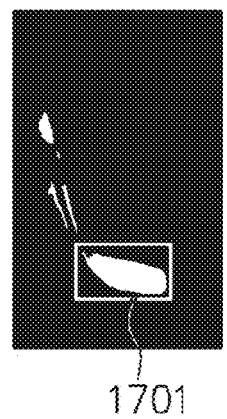
FIG. 17B is a schematic diagram showing detection of plasma blobs when detecting the plasma irradiation position in the conveyance direction of the steel sheet using the image processing device.
Figure 17C:
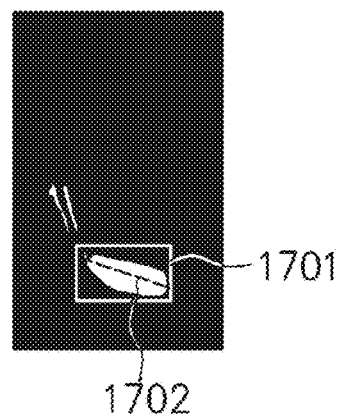
FIG. 17C is a schematic diagram showing calculation of a plasma irradiation axis when detecting the plasma irradiation position in the conveyance direction of the steel sheet using the image processing device.
Figure 18A:
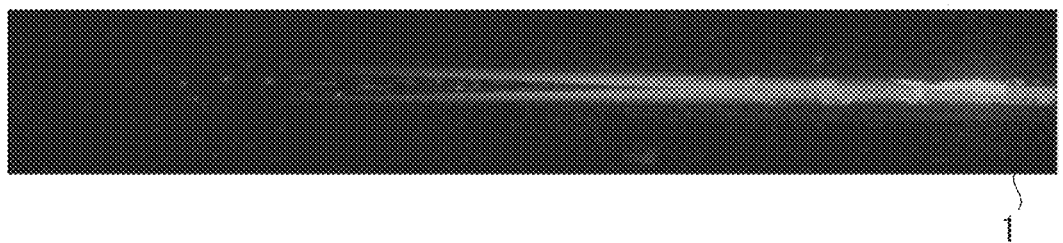
FIG. 18A is a diagram showing an image obtained by capturing a weld zone of conventional electric resistance welding by the conventional technology.
Figure 18B:
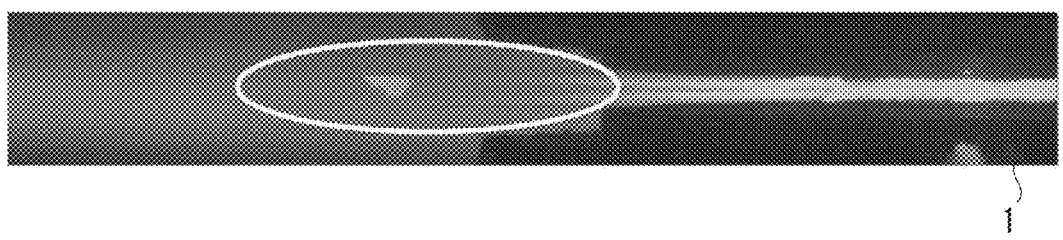
FIG. 18B is a diagram showing an image obtained by capturing the weld zone of the plasma shielded electric resistance welding by the conventional technology.
Figure 18C:
FIG. 18C is a diagram showing a state where a light emission phenomenon between plasma and sputtering and a light emission phenomenon between plasma and a steel material component occur in the image obtained by capturing the weld zone of the plasma shielded electric resistance welding by the conventional technology.

FIG. 17B is a schematic diagram showing detection of plasma blobs by the image processing device 100 in order to detect the plasma irradiation position in the conveyance direction X of the steel sheet 1. FIG. 17C is a schematic diagram showing calculation of a plasma irradiation axis by the image processing device 100 in order to detect the plasma irradiation position in the conveyance direction X of the steel sheet 1.

The image processing device 100 repeatedly executes the image processing shown in FIG. 16 each time when the image data is sent from the third camera 10.

Here, a frame rate of the first camera 4 is 200 fps while a frame rate of the third camera 10 is 40 fps. That is, similar to the second camera 9, five frames can be captured by the first camera 4 while one frame is captured by the third camera 10.

In the description of FIG. 16, an image captured by the first camera 4 is referred to as a weld zone image and an image captured by the third camera 10 is referred to as a plasma image.

In Step S301, the image processing device 100 receives plasma image data sent from the third camera 10.

In Step S302, the image processing device 100 binarizes the processing image which is received in Step S301 as shown in FIG. 17A.

In Step S303, the image processing device 100 performs the labeling processing which allocates a label to each blob for the plasma image which is subjected to binarization in Step 302. In Step S303, the image processing device 100, as shown in FIG. 17B, extracts the blob which has the largest area of the blobs to which the label is allocated as a blob 1701 of plasma.

In Step S304, the image processing device 100 calculates the longer axis of the blob 1701 as an irradiation axis 1702 by a moment computation function as shown in FIG. 17C.

In Step S305, the image processing device 100 obtains a positional relationship of the irradiation axis 1702 with respect to the geometrical V convergence point $V_0$ which is detected in Step S104 of FIG. 8. In Step S304, the image for which the irradiation axis 1702 is calculated is an image captured by the third camera 10. For that reason, five frames of the weld zone image are captured by the first camera 4 until a frame one before the image is captured after the frame is captured. For each of the weld zone images, the geometrical V convergence point $V_0$ is detected in Step S104 shown in FIG. 8.

For that reason, in Step S305, the image processing device 100 calculates an average position of the geometrical V convergence points $V_0$ of the five frames and obtains the positional relationship of the irradiation axis 1702 with respect to the average position.

When the irradiation axis 1702 is separated greatly from the geometrical V convergence points $V_0$, the plasma irradiation position in the conveyance direction X of the steel sheet 1 is not proper.

Although a description has been made mainly on the image processing by the image processing device 100, the plasma irradiation position may be adjusted on the basis of the result of the image processing. For example, when the plasma irradiation position is out of a range of 20 mm to the upstream side of the conveyance direction X of the steel sheet 1 from the geometrical V convergence point $V_0$, the plasma irradiation position is automatically adjusted to be settled in the range.

The field of view of the second camera 9 matches with the field of view of the first camera 4, and thus, it is possible to make the image of plasma captured by the second camera 9 superpose the image of the weld zone 3 captured by the first camera 4. In contrast, since the field of view of the third camera 10 does not match with the field of view of the first camera 4, it is not possible to make the image of plasma captured by the third camera 10 overlap the image of the weld zone 3 captured by the first camera 4.

In a case where it is intended to display plasma of which image is to be captured by the third camera 10 on a monitor along with the weld zone 3, a color camera provided with a CCD image sensor or a CMOS image sensor may be used as the third camera 10. In this case, a filter (band cut filter) which transmits only light having a wavelength of 580 nm to 700 nm (mainly for capturing an image of the butt end 1a of the steel sheet 1) and light having a wavelength of 500 nm or less (mainly for capturing an image of plasma) may be mounted on the third camera 10.

With this, it is possible to detect the plasma irradiation position concerning the conveyance direction X of the steel sheet 1 and display plasma along with the weld zone 3 on the monitor by the image processing. In this case, the blob 1701 of plasma, the irradiation axis 1702, the geometrical V convergence point $V_0$ and the like may be superposed with each other.

However, the above-describe method is only to capture images of both of plasma and the weld zone 3 by the third camera 10 to be displayed on the monitor. It is difficult to analyze the welded state of the weld zone 3 while suppressing the influence by the plasma irradiation on the basis of only the image captured by the third camera 10. In order to analyze the welded state of the weld zone 3 while suppressing the influence by the plasma irradiation, for example, as described in the first embodiment, the optical filter 6 which transmits only light having a wavelength of 900 nm or more is required.

The longer axis direction of the weld zone 3 is different from the longer axis direction of plasma. Furthermore, it is possible to detect the weld zone 3 in the image captured by the third camera 10. For that reason, when the plasma irradiation position in the conveyance direction X of the steel sheet 1 is detected using the image captured by the third camera 10, it is possible to remove the weld zone 3 from the image captured by the third camera 10.

In a case where the weld zone 3 is removed from the image captured by the third camera 10 in a case where the plasma irradiation position and the weld zone 3 overlap, it is not possible to detect the plasma irradiation position for the portion which overlaps the weld zone 3. However, it is possible to detect the plasma irradiation position for the portion which overlaps the weld zone 3 from the plasma irradiation direction and the plasma irradiation position in a portion which does not overlap the weld zone 3.

For that reason, in a case where the weld zone 3 is removed from the image captured by the third camera 10, it is not necessarily required that the third camera 10 be provided with the optical filter 13.

In a case where the image captured by the third camera 10 is superposed on the image of the weld zone 3, a fourth camera having the same field of view as that of the third camera 10 and the same performance as that of the first camera 4 may be additionally used.

An image of the weld zone 3 may be captured from the oblique direction any of the left and right of the conveyance direction X of the steel sheet 1 at a location above the upstream of the conveyance direction X of the steel sheet 1 by the third camera 10 and the fourth camera.

As described above, although preferred embodiments of the present invention have been described in detail, the present invention is not limited to the embodiments, and modifications or the like may be made within the scope of the present invention.

INDUSTRIAL APPLICABILITY

According to the above-described embodiments, it is possible to provide a welded state monitoring system, which is used for plasma shielded electric resistance welding in which electric resistance welding is performed while irradiating a weld zone of a steel sheet with plasma and a welded state monitoring method, the welded state monitoring system and the welded state monitoring method being capable of analyzing a welded state without being affected by plasma.

BRIEF DESCRIPTION OF THE REFERENCE SYMBOLS

1: steel sheet
1a: butt end
1b: upper edge
2: plasma irradiation device
3: weld zone
4: camera, first camera
5: lens
6: optical filter
7: squeeze roll
8: slit
9: second camera
10: third camera
11: branch unit
12: lens
13: optical filter
100: image processing device

What is claimed is:

1. A welded state monitoring system used for plasma shielded electric resistance welding in which an electric resistance welding is performed while irradiating a weld zone of a steel sheet with plasma, the welded state monitoring system comprising:
   a plasma irradiation device which irradiates the weld zone with the plasma;
   a first image capturing device which captures an image of the weld zone from above and has an image sensor capable of detecting light having a wavelength of 850 nm or more;
   a first wavelength region limiting device which limits light incident on the first image capturing device to a wavelength region of 850 nm or more; and
   an image processing device which subjects the image captured by the first image capturing device to image processing and analyzes a welded state of the weld zone.

2. The welded state monitoring system according to claim 1,
   wherein the first wavelength region limiting device limits light incident on the first image capturing device to a wavelength region of 900 nm or more.

3. The welded state monitoring system according to claim 1,
   wherein the image sensor has a quantum efficiency of 10% or more with respect to light in the wavelength region.

4. The welded state monitoring system according to claim 1,
   wherein the first image capturing device has a resolution of 60 μm or less when capturing an image of a range having a width of 100 mm or more.

5. The welded state monitoring system according to claim 1,
   wherein the image processing device obtains a geometrical V convergence point which is a point where both butt ends of the steel sheet which converge in a V shape geometrically intersect each other and a physical abutment point where the both butt ends of the steel sheet which converge in a V shape physically butt against each other.

6. The welded state monitoring system according to claim 1, further comprising:
a second image capturing device which has the same field of view range as that of the first image capturing device; and
a second wavelength region limiting device which limits light incident on the second image capturing device to only light having the wavelength of 500 nm or less,
wherein the image processing device obtains a plasma irradiation position in a width direction of the steel sheet which is a direction orthogonal to a conveyance direction of the steel sheet as a relative position with respect to which the weld zone is set as a reference, on the basis of the image captured by the second image capturing device.

7. The welded state monitoring system according to claim 1, further comprising:
a third image capturing device which is located upstream in the conveyance direction of the steel sheet and captures an image of the weld zone from above the steel sheet and an oblique direction from either of left or right in the conveyance direction of the steel sheet,
wherein the image processing device obtains the plasma irradiation position in the conveyance direction of the steel sheet as a relative position with respect to which the weld zone is set as a reference, on the basis of the image captured by the third image capturing device.

8. The welded state monitoring system according to claim 7, further comprising:
a third wavelength region limiting device which limits light incident on the third image capturing device to only light having a wavelength of 500 nm or less.

9. A welded state monitoring method used for plasma shielded electric resistance welding in which an electric resistance welding is performed while irradiating a weld zone of a steel sheet with plasma, the welded state monitoring method comprising:
capturing an image of the weld zone from above using an image capturing device by limiting light incident on the image capturing device, which is provided with an image sensor capable of detecting light having a wavelength of 850 nm or more, to a wavelength region of 850 nm or more; and
analyzing, using an image processing device, a welded state of the weld zone on the basis of the image captured by the image capturing device.

* * * * *